(12) United States Patent
Mundy et al.

(10) Patent No.: US 6,838,436 B1
(45) Date of Patent: Jan. 4, 2005

(54) INHIBITORS OF PROTEASOMAL ACTIVITY FOR STIMULATING BONE GROWTH

(75) Inventors: Gregory R. Mundy, San Antonio, TX (US); I. Ross Garrett, San Antonio, TX (US); Jorge Gianny Rossini, San Antonio, TX (US)

(73) Assignee: Osteoscreen Inc., San Antonio, TX (US)

(*) Notice: Subject to any disclaimer, the term of this patent is extended or adjusted under 35 U.S.C. 154(b) by 357 days.

(21) Appl. No.: 09/695,807

(22) Filed: Oct. 23, 2000

Related U.S. Application Data

(63) Continuation-in-part of application No. 09/421,545, filed on Oct. 20, 1999, which is a continuation-in-part of application No. 09/361,775, filed on Jul. 27, 1999, now Pat. No. 6,410,512, which is a continuation-in-part of application No. 09/113,947, filed on Jul. 10, 1998, now Pat. No. 6,462,019.

(51) Int. Cl.$^7$ .............................................. A61K 38/00
(52) U.S. Cl. ........................... 514/12; 435/29; 435/69.2
(58) Field of Search .............................. 514/12; 435/29, 435/69.2; 424/92

(56) References Cited

U.S. PATENT DOCUMENTS

| | | | |
|---|---|---|---|
| 4,761,471 A | 8/1988 | Urist | 530/350 |
| 5,280,040 A | 1/1994 | Labroo et al. | 514/457 |
| 5,580,854 A | 12/1996 | Orlowski et al. | 514/18 |
| 5,728,844 A | 3/1998 | Muller et al. | 548/472 |
| 5,767,152 A | 6/1998 | Nielsen et al. | 514/526 |
| 5,780,454 A | 7/1998 | Adams et al. | 514/64 |
| 5,824,643 A | 10/1998 | Pierce et al. | 514/12 |
| 5,910,497 A | 6/1999 | Durette et al. | 514/253 |
| 6,083,690 A | 7/2000 | Harris et al. | 435/6 |
| 6,083,903 A * | 7/2000 | Adams et al. | 514/2 |
| 6,297,217 B1 * | 10/2001 | Adams et al. | 514/18 |
| 6,410,512 B1 * | 6/2002 | Mundy et al. | 514/12 |
| 6,462,019 B1 * | 10/2002 | Mundy et al. | 514/12 |
| 6,492,333 B1 * | 12/2002 | Mundy | 514/18 |

FOREIGN PATENT DOCUMENTS

| | | |
|---|---|---|
| DE | 197 16 713 | 10/1998 |
| EP | 0 931 544 | 7/1999 |
| JP | 05 097697 | 4/1993 |
| JP | 6-25288 A * | 2/1994 |
| WO | WO 90 11366 | 10/1990 |
| WO | WO 92 03125 | 3/1992 |
| WO | WO 93 20859 | 10/1993 |
| WO | WO 95 24211 | 9/1995 |
| WO | WO 95 25533 | 9/1995 |
| WO | WO 96 38590 | 12/1996 |
| WO | WO 97 09315 | 3/1997 |
| WO | WO 97 15308 | 5/1997 |
| WO | WO 97 23457 | 7/1997 |
| WO | WO 97 38699 | 10/1997 |
| WO | WO 97 48694 | 12/1997 |
| WO | WO 98 17267 | 4/1998 |
| WO | WO 98 25460 | 6/1998 |
| WO | WO 0002548 | 1/2000 |

OTHER PUBLICATIONS

Murray E. The Ubiquitin Proteasome System and Cellular Proliferation and Regulation in Osteoblastic Cells. Experimental Cell Research 242(2)460–469, 1998.*

Elofsson M. Towards Subunit Specific Proteasome Inhibitors: Synthesis and Evaluation of Peptide Epoxyketones. Chemistry & Biology 6(11)811–822, 1999.*

Spaltenstein A. Design and Synthesis of Novel Protease Inhibitors. Tetrahedron Letters 37(9)1343–1346, 1996.*

Adams J. Potent and Selective Inhibitors of the Proteasome: Dipeptidyl Boronic Acids. Bioorganic & Medicinal Chemistry Letters 8(4)333–338, 1998.*

U.S. Appl. No. 09/096,631, filed Jun. 12, 1998.

Abu–Amer et al., "NF–kB and Bone: The Breaking Point," Nature Medicine (1997) 3(11):1189–1190.

Adams, J. et al., "Proteasome Inhibitors: A Novel Class of Potent and Effective Antitumor Agents," Cancer Res (1999) 59:2615–2622.

Adams et al., "Chapter 28. Novel Inhibitors of the Proteasome and their Therapeutic Use in Inflammation," Annual Reports in Medicinal Chemistry (1996) 279–288.

Ahmed et al., "Alopecia Universalis Associated with a Mutation in the Human Hairless Gene," SCIENCE (1998) 279:720–724.

Bangham et al., "Diffusion of Univalent Ions Across the Lamellae of Swollen Phospholipids," J Mol Biol (1965) 23:238–252.

Barnes et al., "Nuclear Factor –kB—A Pivotal Transcription Factor in Chronic Inflammatory Diseases," New Engl J Med (1997) 336:1066–1071.

Baumeister et al., "The Proteasome: Paradigm of a Self–Compartmentalizing Protease," CELL(1998) 92:367–380.

Beck et al., "Rapid Publication TGF–$\beta_1$ Induces Bone Closure of Skull Defects," J Bone Miner Res (1991) 6(11):1257–1265.

Bellows et al., "Determination of the Capacity for Proliferation and Differentiation of Osteoprogenitor Cells in the Presence and Absence and Absence of Dexamethasone," Develop Biol (1990) 140:132–138.

(List continued on next page.)

Primary Examiner—Ralph Gitomer
(74) Attorney, Agent, or Firm—Morrison & Foerster LLP

(57) ABSTRACT

The present invention relates to compounds that inhibit the activity of the proteasome or the productions of proteasomal proteins and promote bone formation and are thus useful in treating osteoporosis, bone fracture or deficiency, primary or secondary hyperparathyroidism, periodontal disease or defect, metastatic bone disease, osteolytic bone disease, post-plastic surgery, post-prosthetic joint surgey, and post-dental implantation, in subject where this is desirable.

23 Claims, 1 Drawing Sheet

OTHER PUBLICATIONS

Blessing et al., "Transgenic Mice as a Model to Study the Role of TGF–β–Related Molecules in Hair Follicles," Genes and Develop (1992) 7:204–215.

Burgener et al., "Fluoride Increase Tyrosine Kinase Activity in Osteoblast–like Cells: Regulatory Role for the Stimulation of Cell Proliferation and Pi Transport Across the Plasma Membrane," J Bone Miner Res (1995) 10:164–171.

Caplan, "Mesenchymal Stem Cells" J Orthop Res (1991) 9:641–650.

Casez et al., "Dual–Energy X–Ray Absorptiometry for Measuring Total Bone Mineral Content in the Rat: Study of Accuracy and Precision," Bone and Miner (1994) 26:61–68.

Combaret, L. et al., "Manipulation of the Ubiquitin–Proteasome Pathway in Cachexia: Pentoxifylline Suppresses the Activation of 20S and 26S Proteasoms in Muscles from Tumor–Bearing Rats," Mol Biol Rep (1999) 26:95–101.

Coux, O. et al., "Structure and Functions of the 20S and 26S Proteasomes," An Review Biochem (1996) 65:801–847.

Craiu, A. et al., "Lactacystin and Clasto–Lactacystin β–Lactone Modify Multiple Proteasome β–Subunits and Inhibit Intracellular Protein Degradation and major Histocompatibility Complex Class I Antigen Presentation," J Biol Chem (1997) 272:13437–13445.

Cui et al., "Lovastatin Prevents Steroid–Induced Adipogenesis and Osteoporosis," ASBMR 18th Annual Meeting (Sep. 1996) J Bone Miner Res (1996) 11(S1):S510.

Ducy et al. "Increased Bone Formation in Osteocalcin–deficient Mice," Nature (1996) 382–448–452.

Edelman et al., "Controlled and Modulated Release of Basic Fibroblast Growth Factor," Biomaterials (1991) 12:619–626.

Elofsson et al., Chemistry & Biology (1999) 6:811–822.

Ferretti, "Perspectives of pQct Technology Associated To Biomechanical Studies in Skeletal Research Employing Rat Models," Bone (1995) 17:353S–364S.

Figueiredo–Pereira et al., "A New Inhibitor of the Chymotrypsin–Like Activity of the Multicatalytic Proteinase Complex (20S Proteasome) Induces Accumulation of Ubiquitin–Protein Conjugated in a Neuronal Cell," J Neurochem (1994) 63:1578–1581.

Franzoso et al., "Requirement for NF–kB in Osteoclast and B–Cell Development," Genes and Dev (1997) 11:3482–3496.

Garrett et al, "Specific Inhibitors of the Chymotrypic Component of the Proteasome are Potent Bone Anabolic Agents In Vivo" Journal of Bone and Mineral Research (2000) 15(Suppl.1):S197.

Gat et al., "De Novo Hair Follicle Morphogensis and Hair Tumors in Mice Expressing a Truncated β–Catenin in Skin," CELL (1998) 95:605–614.

Ghosh–Choudhery et al., "Immortalized Murine Osteoblast Derived from BMP 2–T–Antigen Expression Transgenic Mice," Endocrinology (1996) 137:331–339.

Gowan et al., "Actions of Recombinant Interleukin 1, Interleukin 2, and Interferon–γ on Bone Resorption in Vitro," J Immunol (1986) 136:2478–2482.

Groll et al., J. Am. Chem. Soc. (2000) 122:1237–1238.

Guijarro et al. "Lovastatin Inhibits Lipopolysaccharide–induced NF–kB Activation in Human Mesangial Cells," Nephrol Dial Transplant (1996) 11:990–996.

Gupta et al., "Oral Cyclosporine for the Treatment of Alopecia Areata," J Amer Acad of Dermatology (1990) 22(2):242–250.

Hardy et al., "The Secret Life of the Hair Follicle," Trans Genet (1992) 8:55–61.

Harris et al. "Effects of Transforming Growth Factor β on Bone Nodule Formation and Expression of Bone Morphogenetic Protein 2, Osteocalcin, Osteopontin, Alkaline Phosphatase, and Type I Collagen mRNA in Long–Term Cultures of Fetal Rat Calvarial Osteoblasts," J Bone Miner Res (1994) 9:855–863.

Hilt, W. et al., "Proteasomes: Destruction as a Programme," Trans Biochem Sci 91996) 21:96–101.

Iotsova et al., "Osteopetrosis in Mice Lacking NF–kB1 and NF–kB2," Nature Med (1997) 3:1285–1289.

Jensen, T.J. et al., "Multiple Proteolytic Systems, Including the Proteasome, Contribute to CFTR Processing," Cell (1995) 83:129–135.

Kamiya et al., J. Derm. Sci. (1998) 17:54–60.

Kim et al., "Preparation of Multivesicular Liposomes," Biochim Biophys Acta (1983) 728–339–348.

Kimmel et al., "The Effect of Recombinant Human (1–84) or Synthetic Human (1–34) Parathyroid Hormone on the Sleeton of Adult Osteopenic Ovariectomized Rats," Endocrinology (1993) 132:1577–1584.

Ksander et al., "Exogenous Transforming Growth Factor–Beta 2 Enhances Connective Tissue Formation and Wound Strength in Guinea Pig Dermal Wounds Healing by Secondary Intent," Ann Surg (1990) 211(3):288–294.

Laval–Jeantet et al., "Dual–EnergyX–Ray Absorptiometry of the Calcaneus: Comparison with Vertebral Dual–Energy X–Ray Absorptiometry and Quantitative Computed Tomography," Calcif Tissue Intl (1995) 56:14–18.

Law et al., Mol. Cell Biol. (1992) 12:103–111.

Leserman et al., "Targeting to Cells of Fluorescent Liposomes Covalently Coupled With Monoclonal Antibody or Protein A," Nature (1980) 288:602–604.

Liptay et al., "Inhibition of Nuclear Factor Kappa B and Induction of Apoptosis in T–Lymphocytes by Sulfasalazine," Br J Pharmacol (1999) 128(7):1361–1369.

Lutz,"Effects of Cyclosporin A on Hair," Skin Pharmacology (1994) 7:101–104.

Majeska et al., "Maintenance of Parathyroid Hormone Response in Clonal Rat Osteosarcoma Lines," Exp Cell Res (1978) 111:465–467.

Maupin–Furlow, J.A. et al., "A Proteasome from the Methanogenic Archaeon Methanosarcina Thermophila," J Biol Chem (1995) 270:28617–28622.

Mayer et al., "Vesicles of Variable Sizes Produced by a Rapid Extrusion Procedure," Biochim Biophys Acta (1986) 858:161–168.

Meng et al., "Epoxomicin, a Potent and Selective Proteasome Inhibitor, Exhibits In Vivo Antiinflammatory Activity" Proceedings of the National Academy of Sciences of the United States (1999) 96(18):10403–10408.

Mundy et al., Science (1999) 286:1946–1949.

Murray et al., "The Ubiquitin–Proteasome System and Cellular Proliferation and Regulation in Osteoblastic Cells," Experimental Cell Research (1998) 242:460–469.

Olson et al., "Preparation of Liposomes of Defined Size Deistribution by Extrusion Through Polycarbonante Membranes," Biochim Biophys Acta (1979) 557:9–23.

Orford et al., "Serine Phoshorylation–Regulated Ubiquitination and Degradation of β–Catenin," J Biol Chem (1997) 272:24735–24738.

Ozaki et al., "NF–kB Inhibitors Stimulate Apoptosis of Rabbit Mature Osteoclasts and Inhibit Bone Resorption by these Cells," FEBS Letters (1997) 410:297–300.

Pahl et al., "The Immunosupressive Fungal Metabolite Gliotoxin Specifically Inhibits Transcription Factor NF–kB," J Exp Med (1996) 183:1829–1840.

Patent Abstracts of Japan (Aug. 12, 1993) 17:436 (C–1096).

Patent Abstracts of Japan (Jun. 20, 1987) 11:193 (C–430).

Patent Abstracts of Japan (Apr. 25, 1986) 10:112 (C–342).

Peters, J. "Proteasomes: Protein Degradation Machines of the Cell," Trends Biochem Sci (1994) 19:377–382.

Rickard et al., "Induction of Rapid Osteoblast Differentiation in Rat Bone Marrow Stromal Cell Cultures by Dexamethasone and BMP–2," Develop Biol (1994) 161:218–228.

Sampath et al., "Isolation of Osteogenin, an Extracellular Matrix–Associated, Bone–Inductive Protein, by Heparin Affintiy Chromatography," Proc Natl Acad Sci USA (1987) 84:7109–7113.

Sin, N. et al., "Total Synthesis of the Potent Proteasome Inhibitor Epoxomicin: A Useful Tool for Understanding Proteasome Biology," Biorg Med Chem Lett (1999) 9:2283–2288.

Szoka et al., "Procedure for Preparation of Liposomes With Large Internal Aqueous Space and High Capture by Reverse–Phase Evaporation," Proc Natl Acad Sci USA (1978) 75:4194–4198.

Tencer et al., "The Effect of Local Controlled Release of Sodium Fluoride on the Stimulation of Bone Growth," J Biomed Mat Res (1989) 23:571–589.

Vinitsky et al., "Inhibition of the Proteolytic Activity of the Multicatalyic Proteinase Complex (Proteasome) by Substrate–Related Peptidyl Aldehydes," J Biol Chem. (1994) 269(47):29860–29866.

Wahl et al., "Sulfasalazine: A Potent and Specific Inhibitor of Nuclear Kappa B," J Clin Invest (1998) 101(5):1163–1174.

Wang et al., "Lipid Clearing Agents in Steroid–Induced Osteoporosis" J Formos Med Assoc (1995) 94:589–592.

Wojcik et al., "Ubiquitin–Mediated Proteolysis Centers in HeLa Cells: Indication from Studies of an Inhibitor of the Chymotrypsin–Like Activity of the Proteasome," Eur J Cell Biol (1996) 71:311–318.

Wozney, "The Bone Morphogenetic Protein Family as Osteogenesis," Molec Reprod Dev (1992) 32:160–167.

Groll et al., J. Am. Chem. Soc. (2000) 122:1237–1238.

Kamiya et al., J. Derm. Sci. (1998) 17:54–60.

Law et al., Mol. Cell Biol. (1992) 12:103–111.

Mundy et al., Science (1999) 286:1946–1949.

* cited by examiner

INHIBITORS OF PROTEASOMAL ACTIVITY FOR STIMULATING BONE GROWTH

CROSS-REFERENCE TO RELATED APPLICATIONS

This application is a continuation-in-part of U.S. Ser. No. 09/421,545, filed 20 Oct. 1999, now allowed, which is a continuation-in-part of U.S. Ser. No. 09/361,775, filed 27 Jul. 1999, now U.S. Pat. No. 6,410,512, which is a continuation-in-part of U.S. Ser. No. 09/113,947, filed 10 Jul. 1998, now U.S. Pat. No. 6,462,019. The contents of these applications are incorporated herein by reference.

REFERENCE TO A SEQUENCE LISTING

The sequence listing contained in the accompanying compact disc entitled "43272-20026.23 SEQ listing" created on May 5, 2004, 2,048 bytes, is incorporated by reference in its entirety.

1. Technical Field

The invention relates to compositions and methods for use in treating skeletal system disorders in a vertebrate at risk for bone loss, and in treating conditions that are characterized by the need for bone growth, in treating fractures, and in treating cartilage disorders. The invention also relates to enhancing hair density and growth. More specifically, the invention concerns the use of inhibitors of proteasomal activity, e.g., inhibitors of the chymotrypsm-like activity, and inhibitors of NF-κB activity for enhancing hair growth.

2. Background Art

Inhibitors of proteasomal activity, and to some extent inhibitors of NF-κB activity, have two important physiological effects. First, proteasome inhibitors are able to enhance bone formation and are thus useful for treating various bone disorders. Second, both of these inhibitors stimulate the production of hair follicles and are thus useful in stimulating hair growth, including hair density, in subject where this is desirable.

Effect on Bone

Bone is subject to constant breakdown and resynthesis in a complex process mediated by osteoblasts, which produce new bone, and osteoclasts, which destroy bone. The activities of these cells are regulated by a large number of cytokines and growth factors, many of which have now been identified and cloned.

There is a plethora of conditions which are characterized by the need to enhance bone formation or to inhibit bone resorption. Perhaps the most obvious is the case of bone fractures, where it would be desirable to stimulate bone growth and to hasten and complete bone repair. Agents that enhance bone formation would also be useftil in facial reconstruction procedures. Other bone deficit conditions include bone segmental defects, periodontal disease, metastatic bone disease, osteolytic bone disease and conditions where connective tissue repair would be beneficial, such as healing or regeneration of cartilage defects or injury. Also of great significance is the chronic condition of osteoporosis, including age-related osteoporosis and osteoporosis associated with post-menopausal hormone status. Other conditions characterized by the need for bone growth include primary and secondary hyperparathyroidism, disuse osteoporosis, diabetes-related osteoporosis, and glucocorticoid-related osteoporosis.

There are currently no satisfactory pharmaceutical approaches to managing any of these conditions. Bone fractures are still treated exclusively using casts, braces, anchoring devices and other strictly mechanical means. Further bone deterioration associated with post-menopausal osteoporosis has been treated with estrogens or bisphosphonates, which may have drawbacks for some individuals. Although various approaches have been tried, as further discussed below, there remains a need for additions to the repertoire of agents which can be used to treat these conditions.

Treatment of bone or other skeletal disorders, such as those associated with cartilage, can be achieved either by enhancing bone formation or inhibiting bone resorption or both. A number of approaches have been suggested which relate to bone formation.

Bone tissue is an excellent source for factors which have the capacity for stimulating bone cells. Thus, extracts of bovine bone tissue obtained from slaughterhouses contain not only structural proteins which are responsible for maintaining the structural integrity of bone, but also biologically active bone growth factors which can stimulate bone cells to proliferate. Among these latter factors are transforming growth factor β, the heparin-binding growth factors (e.g., acidic and basic fibroblast growth factor), the insulin-like growth factors (e.g., insulin-like growth factor I and insulin-like growth factor II), and a recently described family of proteins called bone morphogenetic proteins (BMPs). All of these growth factors have effects on other types of cells, as well as on bone cells.

The BMPs are novel factors in the extended transforming growth factor β superfamily. Recombinant BMP2 and BMP4 can induce new bone formation when they are injected locally into the subcutaneous tissues of rats (Wozney, J., *Molec Reprod Dev* (1992) 32:160–67). These factors are expressed by normal osteoblasts as they differentiate, and have been shown to stimulate osteoblast differentiation and bone nodule formation in vitro as well as bone formation in vivo (Harris S., et al., *J Bone Miner Res* (1994) 9:855–63). This latter property suggests potential usefulness as therapeutic agents in diseases which result in bone loss.

The cells which are responsible for forming bone are osteoblasts. As osteoblasts differentiate from precursors to mature bone-forming cells, they express and secrete a number of enzymes and structural proteins of the bone matrix, including Type-1 collagen, osteocalcin, osteopontin and alkaline phosphatase. They also synthesize a number of growth regulatory peptides which are stored in the bone matrix, and are presumably responsible for normal bone formation. These growth regulatory peptides include the BMPs (Harris S., et al. (1994), supra). In studies of primary cultures of fetal rat calvarial osteoblasts, BMPs 1, 2, 3, 4, and 6 are expressed by cultured cells prior to the formation of mineralized bone nodules (Harris S., et al. (1994), supra). Like alkaline phosphatase, osteocalcin and osteopontin, the BMPs are expressed by cultured osteoblasts as they proliferate and differentiate.

Although the BMPs are potent stimulators of bone formation in vitro and in vivo, there are disadvantages to their use as therapeutic agents to enhance bone healing. Receptors for the bone morphogenetic proteins have been identified in many tissues, and the BMPs themselves are expressed in a large variety of tissues in specific temporal and spatial patterns. This suggests that BMPs may have effects on many tissues in addition to bone, potentially limiting their usefulness as therapeutic agents when administered systemically. Moreover, since they are peptides, they would have to be administered by injection. These disadvantages impose severe limitations to the development of BMPs as therapeutic agents.

The fluorides, suggested also for this purpose, have a mode of action which may be related to tyrosine phosphorylation of growth factor receptors on osteoblasts, as described, for example, Burgener, et al., *J Bone Min Res* (1995) 10:164–171, but administration of fluorides is associated with increased bone fragility, presumably due to effects on bone mineralization.

Small molecules which are able to stimulate bone formation have been disclosed in PCT applications WO98/17267 published 30 Apr. 1998, WO97/15308 published 1 May 1997 and WO97/48694 published 24 Dec. 1997. These agents generally comprise two aromatic systems spatially separated by a linker. In addition, PCT application WO98/25460 published 18 Jun. 1998 discloses the use of the class of compounds known as statins in enhancing bone formation. U.S. application Ser. No. 09/096,631 filed 12 Jun. 1998 is directed to compounds for stimulating bone growth that are generally isoprenoid pathway inhibitors. The contents of this application, as well as that of the PCT applications cited above, are incorporated herein by reference.

Other agents appear to operate by preventing the resorption of bone. Thus, U.S. Pat. No. 5,280,040 discloses compounds described as useful in the treatment of osteoporosis. These compounds putatively achieve this result by preventing bone resorption.

Wang, G.-J., et al., *J Formos Med Assoc* (1995) 94:589–592 report that certain lipid clearing agents, exemplified by lovastatin and bezafibrate, were able to inhibit the bone resorption resulting from steroid administration in rabbits. There was no effect on bone formation by these two compounds in the absence of steroid treatment. The mechanism of the inhibition in bone resorption observed in the presence of steroids (and the mechanism of the effect of steroid on bone, per se) is said to be unknown.

An abstract entitled "Lovastatin Prevents Steroid-Induced Adipogenesis and Osteoporosis" by Cui, Q., et al., appeared in the Reports of the ASBMR 18th Annual Meeting (September 1996) *J Bone Mineral Res.* (1996)11 (S1):S510 which reports that lovastatin diminished triglyceride vesicles that accumulated when osteoprogenitor cells cloned from bone marrow stroma of chickens were treated in culture with dexamethasone. Lovastatin was reported to diminish the expression of certain mRNAs and to allow the cells to maintain the osteogenic phenotype after dexamethasone treatment, and chickens that had undergone bone loss in the femoral head as a result of dexamethasone treatment were improved by treatment with lovastatin.

These data are, however, contrary to reports that dexamethasone and other inducers, such as BMPs, induce osteoblastic differentiation and stimulate osteocalcin mRNA (Bellows, C. G., et al., *Develop Biol* (1990) 140:132–38; Rickard, D. J., et al., *Develop Biol* (1994) 161:218–28). In addition, Ducy, P., et al., *Nature* (1996) 382:448–52 have recently reported that osteocalcin deficient mice exhibit a phenotype marked by increased bone formation and bones of improved functional quality, without impairment of bone resorption. Ducy, et al., state that their data suggest that osteocalcin antagonists may be of therapeutic use in conjunction with estrogen replacement therapy (for prevention or treatment of osteoporosis).

It has also been shown that lovastatin inhibits lipopolysaccharide-induced NF-κB activation in human mesangial cells. Guijaro, C., et al., *Nephrol Dial Transplant* (1996) 11:6:990–996.

It has recently been shown that mice lacking expression of the transcription factor NF-κB develop an abnormal bone condition, osteopetrosis (the converse of osteoporosis), due to an absence of osteoclast formation (Franzoso, G., et al., *Genes and Dev* (1997) 11:3482–3496; Iotsova, V., et al., *Nature Med* (1997) 3:1285–1289). Osteopetrosis is characterized by such an absence of osteoclast function and the filling in of the marrow cavity with osteocartilagenous material. The mice showed no abnormal osteoblast function. The ability of proteasome inhibitors to stimulate bone growth is unexpected in light of these results, where no effect on osteoblasts was shown since proteasome inhibitors are expected to function as NF-κB inhibitors as well. This is because NF-κB must enter the nucleus to exert its effects on specific target genes, and compounds that inhibit its entry into the nucleus effectively inhibit its activity. Proteasome activity is required for NF-κB translocation. NF-κB is present in the cytoplasm bound to the inhibitory proteins IκBα and IκBβ which prevent its translocation. Translocation occurs when kinases phosphorylate IκBβ to cause its degradation by proteasome activity, thus resulting in its release for entry into the nucleus. Inhibition of proteasome activity prevents this release and thus effectively inhibits NF-κB.

Effect on Hair Growth

Disorders of human hair growth include male pattern baldness, alopecia areota, alopecia induced by cancer chemotherapy and hair thinning associated with aging. These conditions are poorly understood, but nevertheless common and distressing, since hair is an important factor in human social and sexual communication.

Hair follicle regulation and growth are still not well understood, but represent dynamic processes involving proliferation, differentiation and cellular interactions during tissue morphogenesis. It is believed that hair follicles are formed only in early stages of development and not replaced.

Hardy, M. H., et al., *Trans Genet* (1992) 8:55–61 describes evidence that bone morphogenetic proteins (BMPs), members of the TGFβ superfamily, are differentially expressed in hair follicles during development. Harris, S. E., et al., *J Bone Miner Res* (1994) 9:855–863 describes the effects of TGFβ on expression of BMP-2 and other substances in bone cells. BMP-2 expression in mature follicles also occurs during maturation and after the period of cell proliferation (Hardy, et al. (1992, supra). As noted, however, by Blessing, M., et al., *Genes and Develop* (1992) 7:204–215, the precise role functional role of BMP-2 in hair follicle maturation remains unclear.

Approaches to treat baldness abound in the U.S. patent literature. See for example U.S. Pat. No. 5,767,152 (cyanocarboxylic acid derivatives), U.S. Pat. No. 5,824,643 (keratinocyte growth factors) and U.S. Pat. No. 5,910,497 (16-pyrazinyl-substitute-4-aza-androstane 5-alpha.-reductase isozyme 1 inhibitors). There are many others.

Gat, U., et al., *Cell* (1998) 95:605–614 has demonstrated that β-catenin causes adult epithelial cells to create hair follicles, a surprising result in light of the known inability of mature cells to do so. B-Catenin is known to play a role in cell-cell adhesion and growth factor signal transfection. It is also known that after ubiquitination, β-catenin is degraded by the proteasomes. Orford, K., et al., *J Biol Chem* (1997) 272:24735–24738. At least one gene associated with hair growth (or lack thereof) has also been reported. Ahmed, W., et al., *Science* (1998) 279:720–724.

Two accepted agents currently used for the treatment of hair loss are the antihypertensive drug Minoxidil and the 5α-reductase inhibitor Finasteride. Neither is entirely satisfactory. Both suffer from modest efficacy and are inconvenient to administer. A specific, topically active and easy to administer compound with better efficacy than these agents would represent a marked advance.

Proteasomes and NF-κB

The present invention discloses convenient assays for compounds that will be useful in the treatment of bone disorders and in stimulating hair growth. The assays involve inhibition of the activity of the transcription factor NF-κB or of the activity of proteasomal proteases, preferably proteasomal proteases. Compounds which inhibit these activities are generally useful in treating hair growth disorders; proteasome inhibitors enhance bone growth. Compounds that inhibit the production of the transcription factor and these proteases will also be useful in the invention. Their ability to do so can be further confirmed by additional assays.

The proteasome is a noncompartmentalized collection of unrelated proteases which form a common architecture in which proteolytic subunits are self-assembled to form barrel-shaped complexes (for review, see Baumeister, et al., Cell (1998) 92:367–380. The proteasome contains an array of distinct proteolytic activities inside eucaryotic cells. Compounds which inhibit proteasomal activity also reduce NF-κB activity by limiting its capacity to be translocated to the nucleus (Barnes, P. J., et al., New Engl J Med (1997) 336:1066–1071.

DISCLOSURE OF THE INVENTION

The present invention adds to the repertoire of osteogenic and hair growth stimulating agents by providing drugs which would inhibit key proteins and enzymes involved in proteasomal activity and which decrease the activity of the nuclear transcription factor NF-κB, and thus stimulate bone or hair growth. In accordance with the present invention, we have discovered that inhibition of the functions of the proteasomal proteins and, to a lesser extent, of NF-κB in bone cells leads to increased bone growth and to hair follicle formation and stimulation; the effect on hair is also exhibited by inhibitors of NF-κB. Thus, assessing a candidate compound for its ability to inhibit proteasomal proteins or NF-κB provides a useful means to identify bone and hair growth anabolic agents.

The present specification thus provides methods for identification of osteogenic compounds to stimulate bone growth and compounds that stimulate hair growth by assessing their capacity to inhibit proteasome activity and to stimulate hair growth by assessing their ability to inhibit the activity of the transcription factor NF-κB, preferably to inhibit proteasomal activity. Also useful in the methods of the invention are compounds which inhibit the in situ production of the enzymes contained in the proteasome or inhibit the production of NF-κB, preferably of enzymes of the proteasomes. Once a compound found to inhibit these activities has been identified, it can be used in an additional aspect of the invention—a method to stimulate the growth of bone or of hair by contacting suitable cells with the identified compound. The cellular contact may include in vivo administration and the compounds of the invention are thus useful in treating degenerative bone diseases, fractures, dental problems, baldness, alopecia and the like. These methods are performed, according to the present invention, with compounds identified as inhibitors of proteasome activity or inhibitors of the activity of transcription factor NF-κB, preferably inhibitors of the proteasome enzymes, or inhibitors of the production of the proteasome enzymes or of NF-κB, preferably of the proteasome enzymes.

MODES OF CARRYING OUT THE INVENTION

Figure 1:
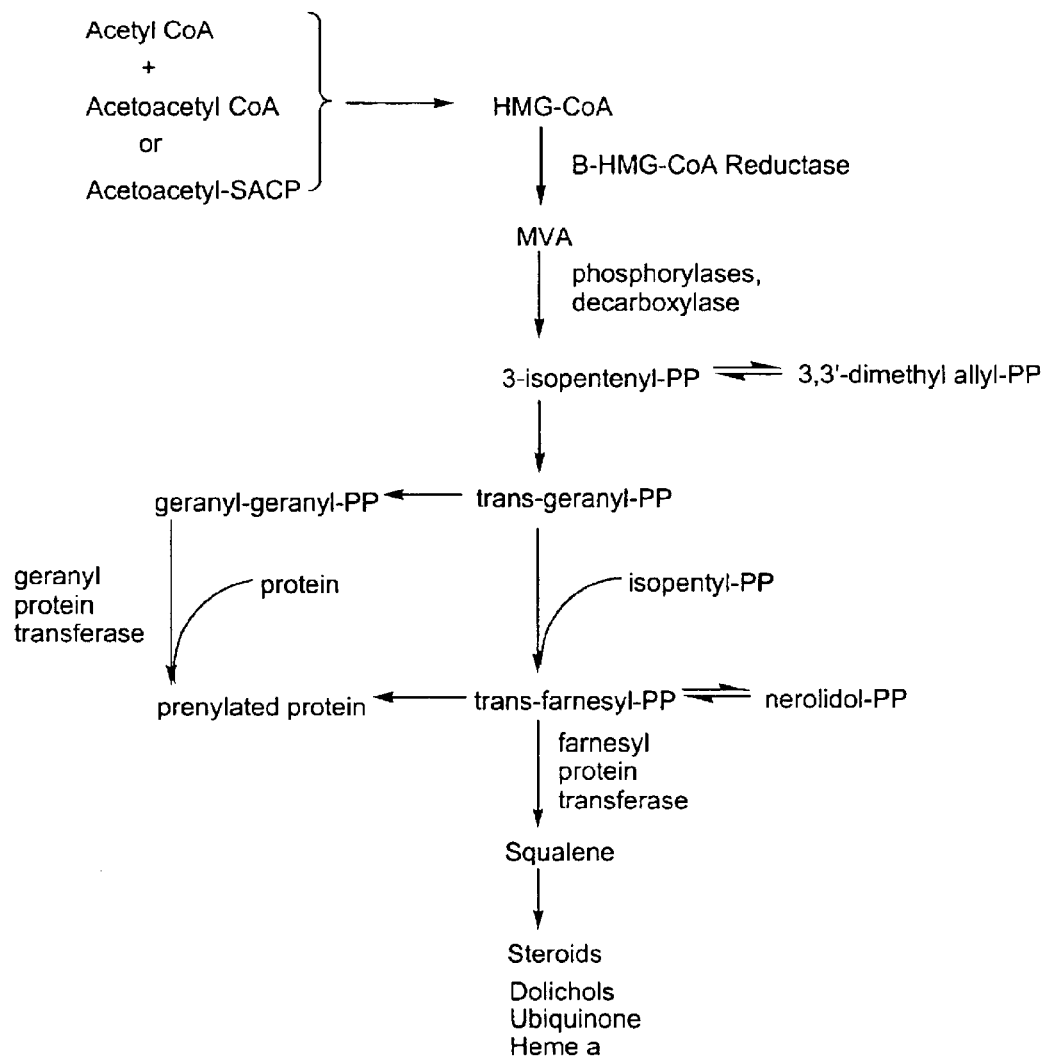
FIG. 1 shows a diagram of the isoprenoid pathway.

In accordance with the present invention, there are provided methods of treating bone defects (including osteoporosis, fractures, osteolytic lesions and segmental bone defects) in subjects suffering therefrom said method comprising administering to said subject, in an amount sufficient to stimulate bone growth, a compound which inhibits proteasomal activity and function or the production of this protein. Inhibitors of NF-κB are also implicated.

Also in accordance with the present invention, there are provided methods of treating disorders of hair growth. Disorders of hair growth may be the result of a defect in the ability of existing hair follicles to extrude hair, or may be the result of a deficiency in the number of hair follicles per se. "Stimulation of hair growth" refers to increasing the volume of hair in a particular area of a subject whether this is the result of an increased rate of growth in length and/or thickness from the same number of hair follicles, growth proceeding from an enhanced number of hair follicles, or both. The number of hair follicles can be enhanced by further activating existing hair follicles or by stimulating the appearance or proliferation of hair follicles in a particular region of the skin.

As employed herein, the term "subject" embraces human as well as other animal species, such as, for example, canine, feline, bovine, porcine, rodent, and the like. It will be understood by the skilled practitioner that the subject is one appropriate to the desirability of stimulating bone growth or hair growth. Thus, in general, for example, stimulation of hair growth will be confined in most instances to animals that would appropriately exhibit such growth.

As used herein, "treat" or "treatment" include a postponement of development of bone deficit symptoms and/or a reduction in the severity of such symptoms that will or are expected to develop. These terms further include ameliorating existing bone or cartilage deficit symptoms, preventing additional symptoms, ameliorating or preventing the underlying metabolic causes of symptoms, preventing or reversing bone resorption and/or encouraging bone growth. Thus, the terms denote that a beneficial result has been conferred on a vertebrate subject with a cartilage, bone or skeletal deficit, or with the potential to develop such deficit.

By "bone deficit" is meant an imbalance in the ratio of bone formation to bone resorption, such that, if unmodified, the subject will exhibit less bone than desirable, or the subject's bones will be less intact and coherent than desired. Bone deficit may also result from fracture, from surgical intervention or from dental or periodontal disease. By "cartilage defect" is meant damaged cartilage, less cartilage than desired, or cartilage that is less intact and coherent than desired. "Bone disorders" includes both bone deficits and cartilage defects.

Representative uses of the compounds identified by the assay of the invention include: repair of bone defects and deficiencies, such as those occurring in closed, open and non-union fractures; prophylactic use in closed and open fracture reduction; promotion of bone healing in plastic surgery; stimulation of bone in-growth into non-cemented prosthetic joints and dental implants; elevation of peak bone mass in pre-menopausal women; treatment of growth deficiencies; treatment of periodontal disease and defects, and other tooth repair processes; increase in bone formation during distraction osteogenesis; and treatment of other skeletal disorders, such as age-related osteoporosis, postmenopausal osteoporosis, glucocorticoid-induced osteoporosis or disuse osteoporosis and arthritis, or any condition that benefits from stimulation of bone formation. The compounds of the present invention can also be useful in repair of congenital, trauma-induced or surgical resection of bone (for instance, for cancer treatment), and in cosmetic surgery. Further, the compounds of the present invention can be used for limiting or treating cartilage defects or disorders, and may be useful in wound healing or tissue repair.

Conditions which would be benefited by "treating" or "treatment" for stimulation of hair growth include male pattern baldness, alopecia caused by chemotherapy, hair thinning resulting from aging, genetic disorders which result in deficiency of hair coverage, and, in animals, providing additional protection from cold temperatures. Thus, while use in humans may be primarily of cosmetic benefit, use in animals may be therapeutic as well.

The compositions of the invention may be administered systemically or locally. For systemic use, the compounds herein are formulated for parenteral (e.g., intravenous, subcutaneous, intramuscular, intraperitoneal, intranasal or transdermal) or enteral (e.g., oral or rectal) delivery according to conventional methods. Intravenous administration can be by a series of injections or by continuous infusion over an extended period. Administration by injection or other routes of discretely spaced administration can be performed at intervals ranging from weekly to once to three times daily. Alternatively, the compounds disclosed herein may be administered in a cyclical manner (administration of disclosed compound; followed by no administration; followed by administration of disclosed compound, and the like). Treatment will continue until the desired outcome is achieved. In general, pharmaceutical formulations will include a compound of the present invention in combination with a pharmaceutically acceptable vehicle, such as saline, buffered saline, 5% dextrose in water, borate-buffered saline containing trace metals or the like. Formulations may further include one or more excipients, preservatives, solubilizers, buffering agents, albumin to prevent protein loss on vial surfaces, lubricants, fillers, stabilizers, etc. Methods of formulation are well known in the art and are disclosed, for example, in *Remington's Pharmaceutical Sciences*, latest edition, Mack Publishing Co., Easton Pa., which is incorporated herein by reference. Pharmaceutical compositions for use within the present invention can be in the form of sterile, non-pyrogenic liquid solutions or suspensions, coated capsules, suppositories, lyophilized powders, transdermal patches or other forms known in the art. Local administration may be by injection at the site of injury or defect, or by insertion or attachment of a solid carrier at the site, or by direct, topical application of a viscous liquid, or the like. For local administration, the delivery vehicle preferably provides a matrix for the growing bone or cartilage, and more preferably is a vehicle that can be absorbed by the subject without adverse effects.

Delivery of compounds herein to wound sites may be enhanced by the use of controlled-release compositions, such as those described in PCT publication WO93/20859, which is incorporated herein by reference. Films of this type are particularly useful as coatings for prosthetic devices and surgical implants. The films may, for example, be wrapped around the outer surfaces of surgical screws, rods, pins, plates and the like. Implantable devices of this type are routinely used in orthopedic surgery. The films can also be used to coat bone filling materials, such as hydroxyapatite blocks, demineralized bone matrix plugs, collagen matrices and the like. In general, a film or device as described herein is applied to the bone at the fracture site. Application is generally by implantation into the bone or attachment to the surface using standard surgical procedures.

In addition to the copolymers and carriers noted above, the biodegradable films and matrices may include other active or inert components. Of particular interest are those agents that promote tissue growth or infiltration, such as growth factors. Exemplary growth factors for this purpose include epidermal growth factor (EGF), fibroblast growth factor (FGF), platelet-derived growth factor (PDGF), transforming growth factors (TGFs), parathyroid hormone (PTH), leukemia inhibitory factor (LIF), insulin-like growth factors (IGFs) and the like. Agents that promote bone growth, such as bone morphogenetic proteins (U.S. Pat. No. 4,761,47; PCT Publication WO90/11366), osteogenin (Sampath, et al., *Proc. Natl. Acad. Sci. USA* (1987) 84:7109–13) and NaF (Tencer, et al., *J Biomed. Mat. Res.* (1989) 23: 571–89) are also preferred. Biodegradable films or matrices include calcium sulfate, tricalcium phosphate, hydroxyapatite, polylactic acid, polyanhydrides, bone or dermal collagen, pure proteins, extracellular matrix components and the like and combinations thereof. Such biodegradable materials may be used in combination with non-biodegradable materials, to provide desired mechanical, cosmetic or tissue or matrix interface properties.

Alternative methods for delivery of compounds of the present invention include use of ALZET osmotic minipumps (Alza Corp., Palo Alto, Calif.); sustained release matrix materials such as those disclosed in Wang, et al. (PCT Publication WO90/11366); electrically charged dextran beads, as disclosed in Bao, et al. (PCT Publication WO92/03125); collagen-based delivery systems, for example, as disclosed in Ksander, et al., *Ann. Surg.* (1990) 211(3): 288–94; methylcellulose gel systems, as disclosed in Beck, et al., *J. Bone Min. Res.* (1991) 6(11):1257–65; alginate-based systems, as disclosed in Edelman, et al., *Biomaterials* (1991) 12:619–26 and the like. Other methods well known in the art for sustained local delivery in bone include porous coated metal prostheses that can be impregnated and solid plastic rods with therapeutic compositions incorporated within them.

The compounds of the present invention may also be used in conjunction with agents that inhibit bone resorption. Antiresorptive agents, such as estrogen, bisphosphonates and calcitonin, are preferred for this purpose. More specifically, the compounds disclosed herein may be administered for a period of time (for instance, months to years) sufficient to obtain correction of a bone deficit condition. Once the bone deficit condition has been corrected, the vertebrate can be administered an anti-resorptive compound to maintain the corrected bone condition. Alternatively, the compounds disclosed herein may be administered with an anti-resorptive compound in a cyclical manner (administration of disclosed compound, followed by anti-resorptive, followed by disclosed compound, and the like).

In additional formulations, conventional preparations such as those described below may be used.

Aqueous suspensions may contain the active ingredient in admixture with pharmacologically acceptable excipients, comprising suspending agents, such as methyl cellulose; and wetting agents, such as lecithin, lysolecithin or long-chain fatty alcohols. The said aqueous suspensions may also contain preservatives, coloring agents, flavoring agents, sweetening agents and the like in accordance with industry standards.

Preparations for topical and local application comprise aerosol sprays, lotions, gels and ointments in pharmaceutically appropriate vehicles which may comprise lower aliphatic alcohols, polyglycols such as glycerol, polyethylene glycol, esters of fatty acids, oils and fats, and silicones. The preparations may further comprise antioxidants, such as ascorbic acid or tocopherol, and preservatives, such as p-hydroxybenzoic acid esters.

Parenteral preparations comprise particularly sterile or sterilized products. Injectable compositions may be provided containing the active compound and any of the well known injectable carriers. These may contain salts for regulating the osmotic pressure.

If desired, the osteogenic agents can be incorporated into liposomes by any of the reported methods of preparing liposomes for use in treating various pathogenic conditions. The present compositions may utilize the compounds noted above incorporated in liposomes in order to direct these compounds to macrophages, monocytes, as well as other cells and tissues and organs which take up the liposomal composition. The liposome-incorporated compounds of the invention can be utilized by parenteral administration, to allow for the efficacious use of lower doses of the compounds. Ligands may also be incorporated to further focus the specificity of the liposomes.

Suitable conventional methods of liposome preparation include, but are not limited to, those disclosed by Bangham, A. D., et al., *J Mol Biol* (1965) 23:238–252, Olson, F., et al., *Biochim Biophys Acta* (1979) 557:9–23, Szoka, F., et al., *Proc Natl Acad Sci USA* (1978) 75:4194–4198, Kim, S., et al., *Biochim Biophys Acta* (1983) 728:339:348, and Mayer, et al., *Biochim Biophys Acta* (1986) 858:161–168.

The liposomes may be made from the present compounds in combination with any of the conventional synthetic or natural phospholipid liposome materials including phospholipids from natural sources such as egg, plant or animal sources such as phosphatidylcholine, phosphatidylethanolamine, phosphatidylglycerol, sphingomyelin, phosphatidylserine, or phosphatidylinositol and the like. Synthetic phospholipids that may also be used, include, but are not limited to: dimyristoylphosphatidylcholine, dioleoylphosphatidylcholine, dipalmitoylphosphatidylcholine and distearoylphosphatidylcholine, and the corresponding synthetic phosphatidylethanolamines and phosphatidylglycerols. Cholesterol or other sterols, cholesterol hemisuccinate, glycolipids, cerebrosides, fatty acids, gangliosides, sphingolipids, 1,2-bis(oleoyloxy)-3-(trimethyl ammonio) propane (DOTAP), N-[1-(2,3-dioleoyl) propyl-N,N,N-trimethylammonium chloride (DOTMA), and other cationic lipids may be incorporated into the liposomes, as is known to those skilled in the art. The relative amounts of phospholipid and additives used in the liposomes may be varied if desired. The preferred ranges are from about 60 to 90 mole percent of the phospholipid; cholesterol, cholesterol hemisuccinate, fatty acids or cationic lipids may be used in amounts ranging from 0 to 50 mole percent. The amounts of the present compounds incorporated into the lipid layer of liposomes can be varied with the concentration of the lipids ranging from about 0.01 to about 50 mole percent.

The liposomes with the above formulations may be made still more specific for their intended targets with the incorporation of monoclonal antibodies or other ligands specific for a target. For example, monoclonal antibodies to the BMP receptor may be incorporated into the liposome by linkage to phosphatidylethanolamine (PE) incorporated into the liposome by the method of Leserman, L., et al., *Nature* (1980) 288:602–604.

Veterinary uses of the disclosed compounds are also contemplated, as set forth above. Such uses would include treatment of bone or cartilage deficits or defects associated with hair or fur in domestic animals, livestock and thoroughbred horses.

The compounds of the present invention may be used to stimulate growth of bone-forming cells or their precursors, or to induce differentiation of bone-forming cell precursors, either in vitro or ex vivo. The compounds described herein may also modify a target tissue or organ environment, so as to attract bone-forming cells to an environment in need of such cells. As used herein, the term "precursor cell" refers to a cell that is committed to a differentiation pathway, but that generally does not express markers or function as a mature, fully differentiated cell. As used herein, the term "mesenchymal cells" or "mesenchymal stem cells" refers to pluripotent progenitor cells that are capable of dividing many times, and whose progeny will give rise to skeletal tissues, including cartilage, bone, tendon, ligament, marrow stroma and connective tissue (see A. Caplan, *J. Orthop. Res.* (1991) 9:641–50). As used herein, the term "osteogenic cells" includes osteoblasts and osteoblast precursor cells. More particularly, the disclosed compounds are useful for stimulating a cell population containing marrow mesenchymal cells, thereby increasing the number of osteogenic cells in that cell population. In a preferred method, hematopoietic cells are removed from the cell population, either before or after stimulation with the disclosed compounds. Through practice of such methods, osteogenic cells may be expanded. The expanded osteogenic cells can be infused (or reinfused) into a vertebrate subject in need thereof. For instance, a subject's own mesenchymal stem cells can be exposed to compounds of the present invention ex vivo, and the resultant osteogenic cells could be infused or directed to a desired site within the subject, where further proliferation and/or differentiation of the osteogenic cells can occur without immunorejection. Alternatively, the cell population exposed to the disclosed compounds may be immortalized human fetal osteoblastic or osteogenic cells. If such cells are infused or implanted in a vertebrate subject, it may be advantageous to "immunoprotect" these non-self cells, or to immunosuppress (preferably locally) the recipient to enhance transplantation and bone or cartilage repair.

As stated above, the compounds of the present invention may also be used to stimulate the growth of hair either by enhancing its rate of formation from existing follicles, stimulating inactive follicles, effecting the production of additional hair follicles or some combination of the foregoing, or by any other mechanism that may or may not presently be understood.

Within the present invention, an "effective amount" of a composition is that amount which produces a statistically significant effect. For example, an "effective amount" for therapeutic uses is the amount of the composition comprising an active compound herein required to provide a clinically significant increase in healing rates in fracture repair; reversal of bone loss in osteoporosis; reversal of cartilage defects or disorders; prevention or delay of onset of osteoporosis; stimulation and/or augmentation of bone formation in fracture non-unions and distraction osteogenesis; increase and/or acceleration of bone growth into prosthetic devices; and repair of dental defects. An "effective amount" for uses in stimulating hair growth is that amount which provides the desired effect in terms of length or density of hair. Such effective amounts will be determined using routine optimization techniques and are dependent on the particular condition to be treated, the condition of the patient, the route of administration, the formulation, and the judgment of the practitioner and other factors evident to those skilled in the art. The dosage required for the compounds of the invention (for example, in osteoporosis where an increase in bone formation is desired) is manifested as a statistically significant difference in bone mass between treatment and control groups. This difference in bone mass may be seen, for example, as a 5–20% or more increase in bone mass in the treatment group. Other measurements of clinically significant increases in healing may include, for example, tests for breaking strength and tension, breaking strength and torsion, 4-point bending, increased connectivity in bone biopsies and other biomechanical tests well known to those skilled in the art. General guidance for treatment regimens is obtained from experiments carried out in animal models of the disease of interest. Differences between successfully treated subjects and controls with regard to stimulation of hair growth can generally be ascertained by direct observation.

The dosage of the compounds of the invention will vary according to the extent and severity of the need for treatment, the activity of the administered compound, the general health of the subject, and other considerations well known to the skilled artisan. Generally, they can be administered to a typical human on a daily basis as an oral dose of about 0.1 mg/kg–1000 mg/kg, and more preferably from about 1 mg/kg to about 200 mg/kg. The parenteral dose will appropriately be 20–100% of the oral dose. While oral administration may be preferable in most instances where the condition is a bone deficit (for reasons of ease, patient acceptability, and the like), alternative methods of administration may be appropriate for selected compounds and selected defects or diseases. While topical administration is generally preferable for stimulating hair growth, as generally only local effects are desired, systemic treatment may be preferable in some instances as well.

Assays for Compounds Useful in the Invention

Assays for assessing the ability of a compound to inhibit proteasomal activity and for inhibitors of NF-κB activity are well known in the art. Two typical, but nonlimiting assays are described below.

Assessment of Proteasomal Activity

Proteasomal inhibition activity is most conveniently measured by the assay described in Example 5 hereinbelow. The assay involves incubating the potential inhibitor with 20S thermophila proteasomes which, in purified form, are commercially available, with a fluorogenic peptide substrate. The presence of an inhibitor will reduce the amount of fluorescence generated by the action of the proteasome fraction on the fluorogenic peptide. This assay is described in further detail in Coux, O., et al., *N Rev Biochem* (1996) 65:801; Adams, J., et al., *Cancer Res* (1999) 59:2615; and Craiu, A., et al., *J Biol Chem* (1997) 272:13437. Further reports are set forth in Hilt, W., et al., *Trans Biochem Sci* (1996) 21:96; Peters, J., *Trends Biochem Sci* (1994) 19:377; Maupin-Furlow, J. A., et al., *J Biol Chem* (1995) 270:28617; and Jensen, T. J., et al., *Cell* (1995) 83:129. Fluorogenic substrates and purified proteasomes are available, for example, from CalBiochem, San Diego, Calif.

NF-κB Activity Assays

Cells are treated with different concentrations of compounds, and nuclear extracts prepared. Briefly, cells are washed with phosphate-buffered saline, and resuspended in lysis buffer (0.6% Nonidet P-40, 150 mM NaCl, 10 mM Tris-HCl, pH 7.9, 1 mM EDTA, 0.5 mM DTT and a cocktail of protease inhibitors (Complete (TM), Boehringer Mannheim). After incubation on ice for 15 min, nuclei are collected by centrifligation. The pellet is resuspended in nuclear extraction buffer (10 mM Hepes, pH 7.9, 420 mM NaCl, 0.1 mM EDTA, 1.5 mM $NgCl_2$, 0.5 mM DTT, protease inhibitors (Complete (TM), Boehringer Mannheim), 25% glycerol), and incubated at 4 degrees C. for 30 min. The supernatant is collected and dialyzed in a buffer containing 10 mM Tris-HCl, pH 7.5, 50 mM NaCl, 5 mM $MgCl_2$, 1 mM EDTA, 1 mM DTT, and 20% glycerol. After dialysis, the nuclear extract is centrifuged to remove precipitated proteins, and aliquots are stored at −70 C. Protein concentration in the nuclear extracts is measured by the method of Bradford using a dye-binding assay kit (Bio-Rad).

The probe for electrophoretic mobility shift assays is a 32P-labeled double-stranded oligonucleotide containing the consensus sequence specific for NF-κB (Promega). Nuclear extracts (5 ug) are pre-incubated in 20-ul reaction mixtures containing 10 mM Tris-HCl, pH 7.5, 50 mM NaCl, 2.5 mM DTT, 0.5 mM EDTA, 1 mM $MgCl_2$, 4% glycerol, and 5 μg of poly (dI-dC). After 10 min at room temperature, 10–20 fmol of probe is added, and incubated further for 20 min. DNA-protein complexes are separated from free oligonucleotides on a 5% polyacrylamide/0.5× TBE gel (45 mM Tris-HCl, 45 mM boric acid, 1 mM EDTA). After electrophoresis, gels are dried and autoradiographed.

Assays for Production Inhibition

Compounds which inhibit the production of the enzymes having proteasomal activity or of NF-κB can be assessed by measuring the level of production of these proteins in the presence and absence of candidate compounds. The levels of production can be readily measured in in vitro systems using, for example, immunoassays for the level of protein produced. The levels of such proteins can also be assessed by utilizing, for example, methionine labeling and size separation of proteins in the cells to be assessed. In order to effect a convenient level of protein production for measurement, it is advantageous to use recombinant expression systems for the relevant enzymes or the NF-κB so that substantial amounts are produced.

Typical approaches to inhibiting the production of NF-κB or proteasome enzymes include the use of antisense technology or formation of triplexes with double-stranded forms of nucleotide sequences relevant in the expression of the genes. In addition, various small molecules may also inhibit this production.

Screening Assays—Bone

The osteogenic activity of the compounds used in the methods of the invention can be verified using in vitro screening techniques, such as the assessment of transcription of a reporter gene coupled to a bone morphogenetic protein-associated promoter or in alternative assays.

ABA Screening Assay

A rapid throughput screening test for compounds that stimulate bone formation by demonstration that they are capable of stimulating expression of a reporter gene linked to a BMP promoter (a surrogate for the production of bone morphogenetic factors that are endogenously produced) is described in U.S. application Ser. No. 08/458,434, filed 2 Jun. 1995, the entire contents of which are incorporated herein by reference. This assay is also described as a portion of a study of immortalized murine osteoblasts (derived from a mouse expressing a transgene composed of a BMP2 promoter driving expression of T-antigen) in Ghosh-Choudhery, N., et al., *Endocrinology* (1996) 137:331–39. In this study, the immortalized cells were stably transfected with a plasmid containing a luciferase reporter gene driven by a mouse BMP2 promoter (−2736/114 bp), and responded in a dose-dependent manner to recombinant human BMP2.

Briefly, the assay utilizes cells transformed permanently or transiently with constructs in which the promoter of a bone morphogenetic protein, specifically BMP2 or BMP4, is coupled to a reporter gene, typically luciferase. These transformed cells are then evaluated for the production of the reporter gene product; compounds that activate the BMP promoter will drive production of the reporter protein, which can be readily assayed. Many thousands of compounds have been subjected to this rapid screening technique, and only a very small percentage are able to elicit a level of expression of reporter gene 5-fold greater than that produced by vehicle. Compounds that activate the BMP promoter fall into groups, where members of each group share certain structural characteristics not present in inactive compounds. The active compounds ("BMP promoter-active compounds" or "active compounds") are useful in promoting bone or cartilage growth, and thus in the treatment of vertebrates in need of bone or cartilage growth.

BMP promoter-active compounds can be examined in a variety of other assays that test specificity and toxicity. For instance, non-BMP promoters or response elements can be linked to a reporter gene and inserted into an appropriate host cell. Cytotoxicity can be determined by visual or microscopic examination of BMP promoter- and/or non-BMP promoter-reporter gene-containing cells, for instance. Alternatively, nucleic acid and/or protein synthesis by the cells can be monitored. For in vivo assays, tissues may be removed and examined visually or microscopically, and optionally examined in conjunction with dyes or stains that facilitate histologic examination. In assessing in vivo assay results, it may also be useful to examine biodistribution of the test compound, using conventional medicinal chemistry/animal model techniques.

Neonatal Mouse Calvaria Assay (In vitro)

An assay for bone resorption or bone formation is similar to that described by Gowen M. & Mundy G., J Immunol (1986) 136:2478–82. Briefly, four days after birth, the front and parietal bones of ICR Swiss white mouse pups are removed by microdissection and split along the sagittal suture. In an assay for resorption, the bones are incubated in BGJb medium (Irvine Scientific, Santa Ana, Calif.) plus 0.02% (or lower concentration) β-methylcyclodextrin, wherein the medium also contains test or control substances. The medium used when the assay is conducted to assess bone formation is Fitton and Jackson Modified BGJ Medium (Sigma) supplemented with 6 $\mu$g/ml insulin, 6 $\mu$g/ml transferrin, 6 ng/ml selenous acid, calcium and phosphate concentrations of 1.25 and 3.0 mM, respectively, and ascorbic acid to a concentration of 100 $\mu$g/ml is added every two days. The incubation is conducted at 37° C. in a humidified atmosphere of 5% $CO_2$ and 95% air for 96 hours.

Following this, the bones are removed from the incubation media and fixed in 10% buffered formalin for 24–48 hours, decalcified in 14% EDTA for 1 week, processed through graded alcohols; and embedded in paraffin wax. Three Am sections of the calvaria are prepared. Representative sections are selected for histomorphometric assessment of bone formation or bone resorption. Bone changes are measured on sections cut 200 $\mu$m apart. Osteoblasts and osteoclasts are identified by their distinctive morphology.

Other auxiliary assays can be used as controls to determine non-BMP promoter-mediated effects of test compounds. For example, mitogenic activity can be measured using screening assays featuring a serum-response element (SRE) as a promoter and a luciferase reporter gene. More specifically, these screening assays can detect signaling through SRE-mediated pathways, such as the protein kinase C pathway. For instance, an ostcoblast activator SRE-luciferase screen and an insulin mimetic SRE-luciferase screen are useful for this purpose. Similarly, test compound stimulation of cAMP response element (CRE)-mediated pathways can also be assayed. For instance, cells transfected with receptors for PTH and calcitonin (two bone-active agents) can be used in CRE-luciferase screens to detect elevated cAMP levels. Thus, the BMP promoter specificity of a test compound can be examined through use of these types of auxiliary assays.

In vivo Assay of Effects of Compounds on Murine Calvarial Bone Growth

Male ICR Swiss white mice, aged 4–6 weeks and weighing 13–26 gm, are employed, using 4–5 mice per group. The calvarial bone growth assay is performed as described in PCT application WO95/24211, incorporated by reference. Briefly, the test compound or appropriate control vehicle is injected into the subcutaneous tissue over the right calvaria of normal mice. Typically, the control vehicle is the vehicle in which the compound was solubilized, and is PBS containing 5% DMSO or is PBS containing Tween (2 $\mu$l/10 ml). The animals are sacrificed on day 14 and bone growth measured by histomorphometry. Bone samples for quantitation are cleaned from adjacent tissues and fixed in 10% buffered formalin for 24–48 hours, decalcified in 14% EDTA for 1–3 weeks, processed through graded alcohols; and embedded in paraffin wax. Three to five $\mu$m sections of the calvaria are prepared, and representative sections are selected for histomorphometric assessment of the effects on bone formation and bone resorption. Sections are measured by using a camera lucida attachment to trace directly the microscopic image onto a digitizing plate. Bone changes are measured on sections cut 200 $\mu$m apart, over 4 adjacent 1×1 mm fields on both the injected and noninjected sides of the calvaria. New bone is identified by its characteristic woven structure, and osteoclasts and osteoblasts are identified by their distinctive morphology. Histomorphometry software (OsteoMeasure, Osteometrix, Inc., Atlanta) is used to process digitizer input to determine cell counts and measure areas or perimeters.

Typical treatment regimens for testing utilize application of the compound to be tested over several days of repeated administration.

Additional In Vivo Assays—Bone

Lead compounds can be further tested in intact animals using an in vivo, dosing assay. Prototypical dosing may be accomplished by subcutaneous, intraperitoneal or oral administration, and may be performed by injection, sustained release or other delivery techniques. The time period for administration of test compound may vary (for instance, 28 days as well as 35 days may be appropriate). An exemplary, in vivo oral or subcutaneous dosing assay may be conducted as follows:

In a typical study, 70 three-month-old female Sprague-Dawley rats are weight-matched and divided into seven groups, with ten animals in each group. This includes a baseline control group of animals sacrificed at the initiation of the study; a control group administered vehicle only; a PBS-treated control group; and a positive control group administered a compound (non-protein or protein) known to promote bone growth. Three dosage levels of the compound to be tested are administered to the remaining three groups.

Briefly, test compound, positive control compound, PBS, or vehicle alone is administered subcutaneously once per day for 35 days. All animals are injected with calcein nine days and two days before sacrifice (two injections of calcein administered each designated day). Weekly body weights are determined. At the end of the 35-day cycle, the animals are weighed and bled by orbital or cardiac puncture. Serum calcium, phosphate, osteocalcin, and CBCs are determined. Both leg bones (femur and tibia) and lumbar vertebrae are removed, cleaned of adhering soft tissue, and stored in 70% ethanol for evaluation, as performed by peripheral quantitative computed tomography (pQCT; Ferretti, J., Bone (1995) 17:353S-64S), dual energy X-ray absorptiometry (DEXA; Laval-Jeantet A., et al., Calcif Tissue Intl (1995) 56:14–18; J. Casez, et al., Bone and Mineral (1994) 26:61–68) and/or histomorphometry. The effect of test compounds on bone remodeling can thus be evaluated.

Lead compounds can also be tested in acute ovariectomized animals (prevention model) using an in vivo dosing assay. Such assays may also include an estrogen-treated group as a control. An exemplary subcutaneous dosing assay is performed as follows:

In a typical study, 80 three-month-old female Sprague-Dawley rats are weight-matched and divided into eight groups, with ten animals in each group. This includes a baseline control group of animals sacrificed at the initiation of the study; three control groups (sham ovariectomized (sham OVX)+vehicle only; ovariectomized (OVX)+vehicle only; PBS-treated OVX); and a control OVX group that is administered a compound known to promote bone growth. Three dosage levels of the compound to be tested are administered to the remaining three groups of OVX animals.

Since ovariectomy (OVX) induces hyperphagia, all OVX animals are pair-fed with sham OVX animals throughout the 35 day study. Briefly, test compound, positive control compound, PBS, or vehicle alone is administered orally or subcutaneously once per day for 35 days. Alternatively, test compound can be formulated in implantable pellets that are implanted for 35 days, or may be administered orally, such as by gastric gavage. All animals, including sham OVX/vehicle and OVX/vehicle groups, are injected intraperitoneally with calcein nine days and two days before sacrifice (two injections of calcein administered each designated day, to ensure proper labeling of newly formed bone). Weekly body weights are determined. At the end of the 35-day cycle, the animals' blood and tissues are processed as described above.

Lead compounds may also be tested in chronic OVX animals (treatment model). An exemplary protocol for treatment of established bone loss in ovariectomized animals that can be used to assess efficacy of anabolic agents may be performed as follows. Briefly, 80 to 100 six month old female, Sprague-Dawley rats are subjected to sham surgery (sham OVX) or ovariectomy (OVX) at time 0, and 10 rats are sacrificed to serve as baseline controls. Body weights are recorded weekly during the experiment. After approximately 6 weeks (42 days) or more of bone depletion, 10 sham OVX and 10 OVX rats are randomly selected for sacrifice as depletion period controls. Of the remaining animals, 10 sham OVX and 10 OVX rats are used as placebo-treated controls. The remaining OVX animals are treated with 3 to 5 doses of test drug for a period of 5 weeks (35 days). As a positive control, a group of OVX rats can be treated with an agent such as PTH, a known anabolic agent in this model (Kimmel, et al, Endocrinology (1993) 132:1577–84). To determine effects on bone formation, the following procedure can be followed. The femurs, tibiae and lumbar vertebrae 1 to 4 are excised and collected. The proximal left and right tibiae are used for pQCT measurements, cancellous bone mineral density (BMD) (gravimetric determination), and histology, while the midshaft of each tibiae is subjected to cortical BMD or histology. The femurs are prepared for pQCT scanning of the midshaft prior to biomechanical testing. With respect to lumbar vertebrae (LV), LV2 are processed for BMD (pQCT may also be performed); LV3 are prepared for undercalcified bone histology; and LV4 are processed for mechanical testing.

Assays for Hair Growth

The ability of the compositions of the invention to stimulate hair growth was, surprisingly, discovered in the course of assessing their ability to stimulate the growth of bone. Accordingly, set forth below is the bone growth assay that led to the discovery of the hair growth stimulating ability of these compounds.

In Vivo Assay of Effects of Compounds on Hair Follicles Proliferation and Hair Growth The assay described above to assess the effect of compounds on calvarial bone growth can also be used to assess the ability of compounds to stimulate hair growth. The test compound or appropriate control vehicle is applied to the upper and lower back of male ICR Swiss white mice either topically or by subcutaneous injection. The vehicle is selected as appropriate for the compound to be tested and for the route of administration. Optionally, the hair in the test area may be removed prior to administration. After a suitable interval, typically 7 days, the mice are anesthetized and a biopsy of the dorsal treatment area is taken using a 6 mm dermal punch. The specimens are fixed in 10% buffered formalin and imbedded in paraffin wax, and sectioned and stained to observe hair follicles. In addition, photography can be used to observe and record hair growth; typically such growth is observed after 14–18 days. After a suitable interval, typically 21 days, the animals may be euthanized and the hair analyzed for fiber analysis and the tissue from the treatment area analyzed for quantitation of hair follicles.

In more detail, male ICR Swiss white mice, aged 4–6 weeks and weighing 13–26 gm, are employed, using 4–5 mice per group. The calvarial bone growth assay is performed as described above. Briefly, the test compound or appropriate control vehicle is injected into the subcutaneous tissue over the right calvaria of normal mice. Typically, the control vehicle is the vehicle in which the compound was solubilized, and is PBS containing 5% DMSO or is PBS containing Tween (2 $\mu$l/10 ml). The animals are sacrificed on day 14 and bone growth measured by histomorphometry. Bone samples for quantitation are cleaned from adjacent tissues and fixed in 10% buffered formalin for 24–48 hours, decalcified in 14% EDTA for 1–3 weeks, processed through graded alcohols; and embedded in paraffin wax. Three to five Am sections of the calvaria are prepared, and representative sections are selected for histomorphometric assessment of the effects on bone formation and bone resorption. Sections are measured by using a camera lucida attachment to trace directly the microscopic image onto a digitizing plate. Bone changes are measured on sections cut 200 $\mu$m apart, over 4 adjacent 1×1 mm fields on both the injected and noninjected sides of the calvaria. New bone is identified by its characteristic woven structure, and osteoclasts and osteoblasts are identified by their distinctive morphology. Histomorphometry software (OsteoMeasure, Osteometrix, Inc., Atlanta) is used to process digitizer input to determine cell counts and measure areas or perimeters.

Typical treatment regimens for testing utilize application of the compound to be tested over several days of repeated administration.

Nature of the Compounds Useful in the Invention

The compounds useful in the methods and compositions of the invention are inhibitors of proteasomal activity, of the transcription factor NF-κB, preferably both. Known inhibitors of these activities can be ascertained from the literature or compounds can be tested for these activities using assays known in the art. In addition, inhibitors which lower the level of effective expression of the nucleotide sequence encoding the enzymes that have proteasomal activity or of the nucleotide sequence encoding NF-κB can be assessed and used in the invention methods.

The compounds thus identified, which are used according to the method of the invention as it relates to treating bone defects, however, preferably do not include compounds that inhibit the isoprenoid pathway, such as the statins. A description of these excluded compounds can be found in WO98/25460 and in U.S. Ser. No. 09/096,631, both cited above and incorporated herein by reference. For convenience, the isoprenoid pathway referred to is set forth herein in FIG. 1. One class of compounds which are inhibitors are the statins which have the formula

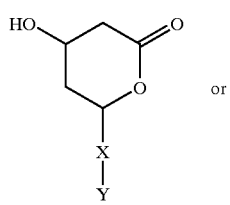
(1)

or

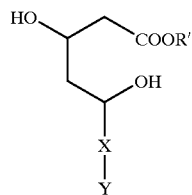
(2)

wherein X in each of formulas (1) and (2) represents a substituted or unsubstituted alkylene, alkenylene, or alkynylene linker of 2–6C;

Y represents one or more carbocyclic or heterocyclic rings wherein, when Y comprises two or more rings, said rings may be fused; and R' represents a cation, H or a substituted or unsubstituted alkyl group of 1–6C; and the dotted lines represent optional π-bonds.

These compounds may, however, be used in the method of the invention as it relates to the stimulation of hair growth.

| Compounds known to be proteasome or NF-κB inhibitors include: | |
|---|---|
| Proteasome Inhibitors | |
| PSI | N-carbobenzoyl-Ile-Glu-(OtBu)-Ala-Leu-CHO |
| MG-132 | N-carbobenzoyl-Leu-Leu-Leu-CHO |
| MG-115 | N-carbobenzoyl-Leu-Leu-Nva-CHO |
| MG-101 or Calpain Inh I | N-Acetyl-Leu-Leu-norLeu-CHO |
| ALLM | N-Acetyl-Leu-Leu-Met-CHO |
| | N-carbobenzoyl-Gly-Pro-Phe-Leu-CHO (SEQ ID NO:1) |
| | N-carbobenzoyl-Gly-Pro-Ala-Phe-CHO (SEQ ID NO:2) |
| | N-carbobenzoyl-Leu-Leu-Phe-CHO |
| | N-carbobenzoyl-Leu-Ala-Leu-CHO |
| Gliotoxin | 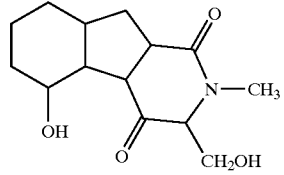 |
| SN50 | NLS of NF-κB MW 2781 |
| Bay 11-7082 | 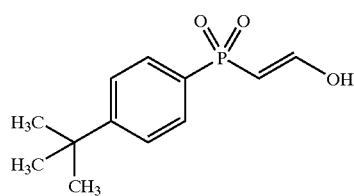 |
| Capsaicin | 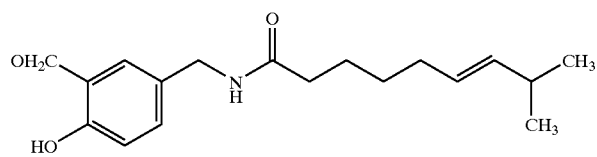 |
| PDTC | 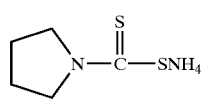 |

-continued
Compounds known to be proteasome or NF-κB inhibitors include:
Proteasome Inhibitors
ALLN
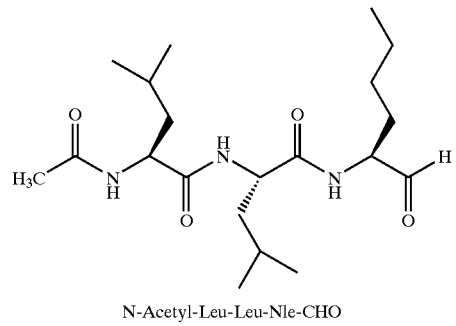
N-Acetyl-Leu-Leu-Nle-CHO
MG-262
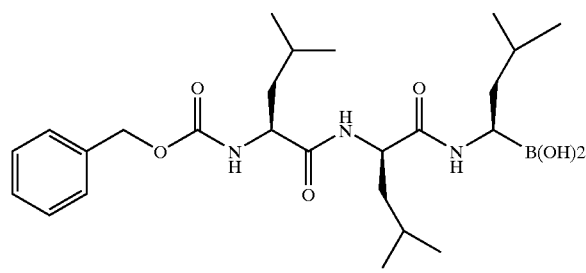
PPM-18
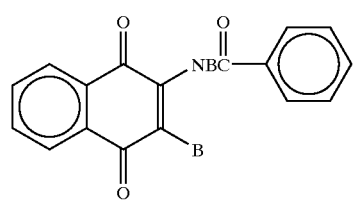
Cyclosporin A
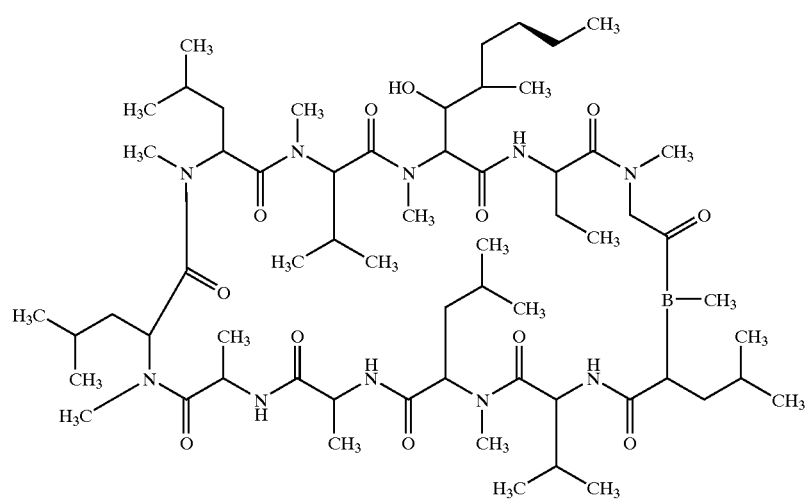

-continued

Compounds known to be proteasome or NF-κB inhibitors include:

Proteasome Inhibitors

Epoxomicin

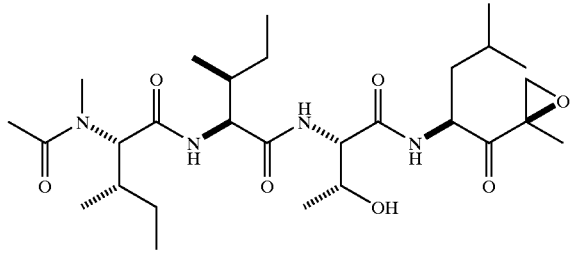

See, for example, Vinitsky, A., et al., *J Biol Chem* (1994) 269:29860–29866; Figueiredo-Pereira, M. E., et al., *J Neurochem* (1994) 63:1578–1581; Wojeik, C., et al., *Eur J Cell Biol* (1996) 71:311–318.

The compound can

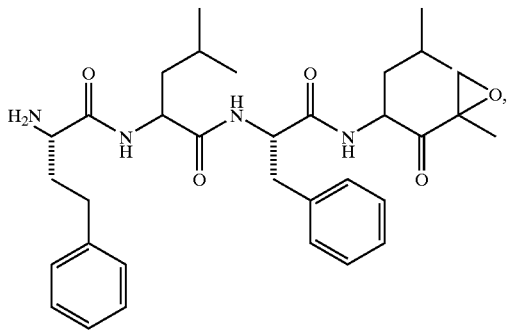

epoxomicin, pyrazylcaarbonyl-Phe-Leu-Boronate (PS-341), tri-leucine vinyl sulfone (NLVS), N-carbobenzoyl-Ile-Glu-(OtBu)-Ala-Leu-CHO (PSI) epoxide, lactacystin, or a peptidyl aldehyde.

In the foregoing list, lactacystin is known to be an irreversible inhibitor of proteasome activity. It binds to the β catalytic subunit and is a specific inhibitor of the 20S proteasome. It also irreversibly inhibits NF-κB.

SN50 is the NLS (nuclear localization sequence) of p50 plus the hydrophobic region of K-FGF. It inhibits the translocation of the NF-κB active complex to the nucleus.

Certain peptidyl epoxy ketones such as EST and the epoxide of PSI are irreversible inhibitors of the proteasomes.

A particularly useful epoxy ketone is epoxomicin, a natural product whose structure is shown in the above table. It appears to be a highly specific and irreversible inhibitor of the proteasome which has been shown to modify, covalently, at least four catalytic subunits of the 20S proteasome. It does not appear to inhibit nonproteasomal proteases such as cathepsin B, papain, chymotrypsin or calpain at concentrations up to 50 μM. Epoxomicin also effectively NF-κB activation in vitro. The synthesis of epoxomicin is described by Sin, N., et al., *Biorg Med Chem Lett* (1999) 9:2283–2288.

MG-132 shows activity against the chymotryptic activity of the 20S protein without affecting its ATPase or isopeptidase activity and reversibly inhibits NF-κB activity. MG-115 and MG-341 show similar activities to MG-132. Various other inhibitors of NF-κB are less active in the ABA assay. These include capsaicin, curcumin, and resiniferatoxin. Other compounds known to inhibit NF-κB are gliotoxin and PDTC (1-pyrrolidine carbothiotic acid). Various other compounds such as BAY-11-7082 and BAY-11-7085 as well as calyculin-A inhibit phosphorylation of NF-κB. Calpain inhibitor inhibits calpain 1 and the proteasome; other compounds such as olomoucine and roscovitine inhibit cdk2 and/or cdk5.

An additional compound shown to be a proteasome inhibitor is pentoxyfilline (PTX). Combaret, L., et al., *Mol Biol Rep* (1999)26:95–101. It is active in the in vitro calvarial assay described above.

As set forth above, in preferred embodiments of the methods of the invention, the identified compounds used in treatment of bone disorders are other than statins and other compounds that inhibit the isoprenoid pathway, typically as shown in FIG. 1. In other preferred embodiments, also excluded from use in the methods of treatment of bone disorders of the present invention, are compounds described in PCT applications WO98/17267, WO97/15308, and WO97/48694 cited and incorporated herein by reference hereinabove. However, the use of these compounds in the method to stimulate hair growth according to the invention is not excluded.

One particular type of compounds that can be used in the methods and pharmaceutical compositions for treating pathological dental conditions or degenerative joint conditions in a vertebrate animal are compounds that inhibit the chymotrypsin-like activity of the proteasome. Any known chymotrypsin-like activity inhibitors can be used. For example, the compound used can have a "warhead," i.e., a functional group, that reacts with the chymotrypsin-like site of the proteasome. Exemplary "warheads" include an epoxide that is capable of forming a morpholino ring with the threonine residue of the chymotrypsin-like catalytic site of the proteasome (Elofsson, et al., *Chemistry & Biology*, 6:811–822 (1999); and Groll, et al., *J Am. Chem. Soc.,* 122:1237–1238 (2000)), or a group that can react irreversibly with the active site of the chymotrypsin-like activity such as a —B(OR)$_2$ group, a —S(OR)$_2$ group, or a —SOOR group, wherein R is H, an alkyl (C$_{1-6}$) or an aryl (C$_{1-6}$). In one specific embodiment, the compound used is a peptide, or an analog thereof, having the above-described "warhead." Preferably, the peptide has at least 3 amino acids.

One example of the chymotrypsin-like activity inhibitors that can be used is a peptide α', β'-epoxyketone. The length of the peptide can be 3, but is preferably at least 4 amino acids. The C-terminus amino acid of the peptide α', β'-epoxyketone is preferably a hydrophobic amino acid such as leucine or phenylalanine. More preferably, the peptide α', β'-epoxyketone used has the following formula:

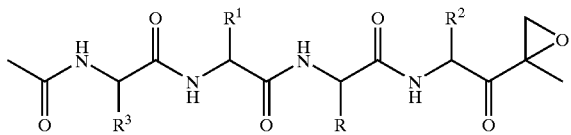

wherein R, R¹, R² and R are independently, for example,

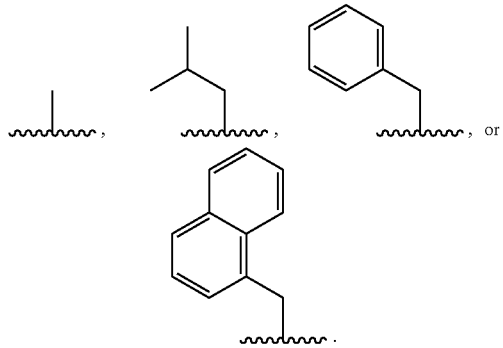

Preferably, the peptide α', β'-epoxyketone has the following stereo-configuration:

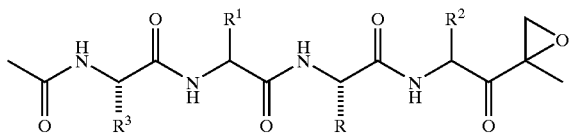

In the exemplary compounds having the above formula R² and R³ are the side chains of leucine, isoleucine, valine or phenyl alanine and these include compound 1

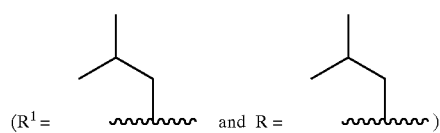

compound 2

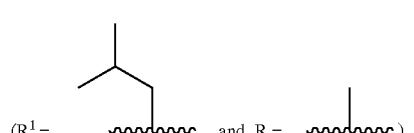

compound 3

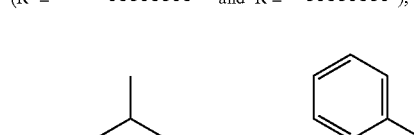

compound 4

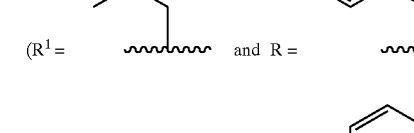

compound 5

(R¹ = ⁓⁓⁓ and R = ⁓⁓⁓), compound 6

(R¹ = ⁓⁓⁓ and R = ⁓⁓⁓) and compound 7

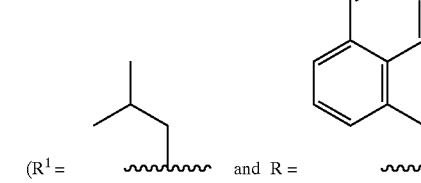

(R¹ = ⁓⁓⁓ and R = ⁓⁓⁓).

Another example of the peptide α', β'-epoxyketone that can be used has the following formula:

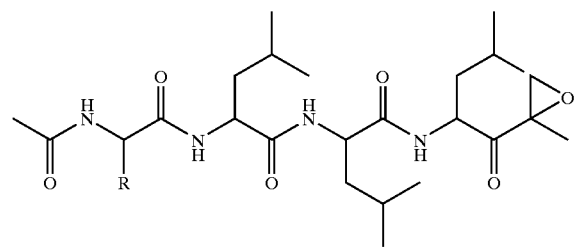

wherein R can be, for example,

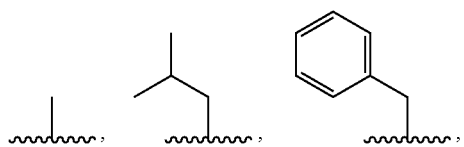

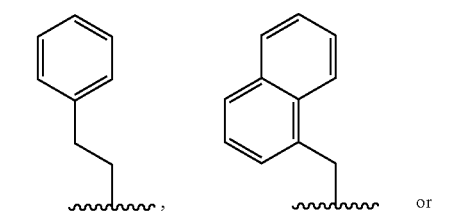

or

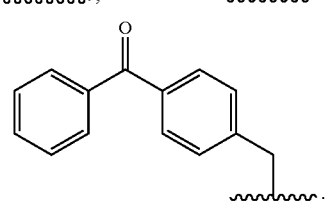

Preferably, the peptide α', β'-epoxyketone has the following stereo-configuration:

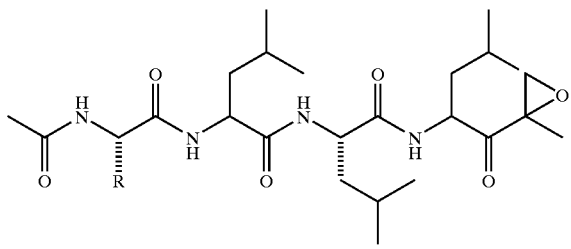

More preferably, the peptide α', β'-epoxyketone used is:

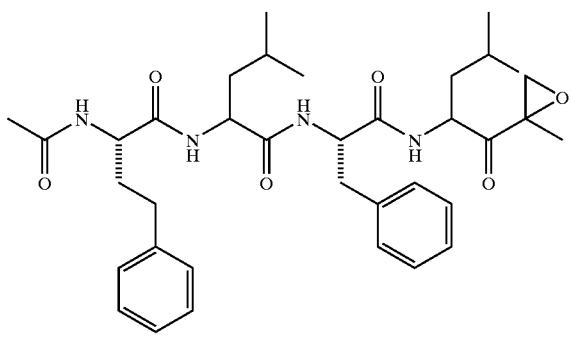

Still another example of the proteasome inhibitors that can be used has the following formula:

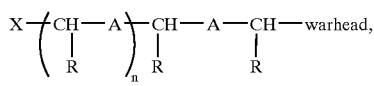

wherein the warhead reacts irreversibly with the catalytic chymotrypsin site of the proteasome;

A is independently CO—NH or isostere thereof;

R is independently a hydrocarbyl;

X is a polar group; and n=0–2.

Optionally, the R group can contain a substituted group such as a halo group, —OR, —SR, —NR$_2$, =O, —COR, —OCOR, —NHCOR, —NO$_2$, —CN, or —CF$_3$. Also optionally, X can be a protected group.

Alternatively, the following compounds can also be used:

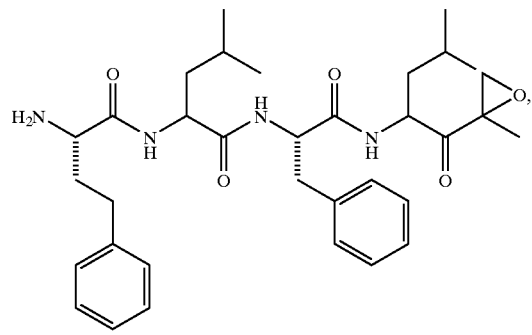

epoxomicin, PS-341, NLVS, lactacystin, PTX, or a peptidyl aldehyde. Particularly preferred is the epoxide of PSI.

In addition, proteasome inhibitors disclosed in U.S. Pat. No. 5,780,454, which is incorporated by reference in its entirety herein, can be used. Especially, the proteasome inhibitors having formula (1b) or (2b), as disclosed in U.S. Pat. No. 5,780,454, can be used.

Compounds that inhibit the trypsin-like or PGPH activity of the proteasome can be used in the methods and pharmaceutical compositions for stimulating hair growth in a mammalian subject. Preferably, the compound used is lactacystin or a peptidyl aldehyde.

Other compounds that can be used in the present methods and pharmaceutical compositions for treating pathological dental conditions or degenerative joint conditions in a vertebrate animal or for stimulating hair growth in a mammalian subject include, but are not limited to, sulfasalazine (Liptay, et al., Br. *J Pharmacol,* 128(7):1361–9 (1999)); and Wahl, et al., *J Clin. Invest.,* 101(5):1163–74 (1998)) and calpain inhibitor II.

The following examples are intended to illustrate but not to limit the invention.

EXAMPLE 1

High throughput Screening

Thousands of compounds have been tested in the assay system set forth in U.S. Ser. No. 08/458,434, filed 2 Jun. 1995, and incorporated herein by reference. Representative compounds of the invention gave positive responses, while the majority of (unrelated) compounds are inactive. In this screen, the standard positive control was the compound 59-0008 (also denoted "OS8"), which is of the formula:

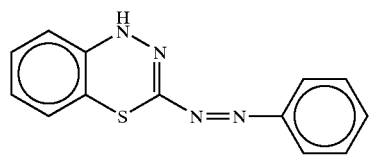

"OS8"

In more detail, the 2T3-BMP-2-LUC cells, a stably transformed osteoblast cell line described in Ghosh-Choudhury et al. *Endocrinology* (1996) 137:331–39, referenced above, was employed. The cells were cultured using α-MEM, 10% FCS with 1% penicillin/streptomycin and 1% glutamine ("plating medium"), and were split 1:5 once per week. For the assay, the cells were resuspended in a plating medium containing 4% FCS, plated in microtiter plates at a concentration of 5×10$^3$ cells (in 50 μl)/well, and incubated for 24 hours at 37° C. in 5% CO$_2$. To initiate the assay, 50 μl of the test compound or the control in DMSO was added at 2× concentration to each well, so that the final volume was 100 μl. The final serum concentration was 2% FCS, and the final DMSO concentration was 1%. Compound 59-0008 (10 μM) was used as a positive control.

The treated cells were incubated for 24 hours at 37° C. and 5% CO$_2$. The medium was then removed, and the cells were rinsed three times with PBS. After removal of excess PBS, 25 μl of 1× cell culture lysing reagent (Promega #E153A) was added to each well and incubated for at least ten minutes. Optionally, the plates/samples could be frozen at this point. To each well was added 50 μl of luciferase substrate (Promega #E152A; 10 ml Promega luciferase assay buffer per 7 mg Promega luciferase assay substrate). Luminescence was measured on an automated 96-well luminometer, and was expressed as either picograms of luciferase activity per well or as picograms of luciferase activity per microgram of protein.

In this assay, compound 59-0008 (3-phenylazo-1H-4,1,2-benzothiadiazine) exhibits a pattern of reactivity which is maximal at a concentration of approximately 3–10 μM. Accordingly, other tested compounds can be evaluated at various concentrations, and the results compared to the results obtained for 59-0008 at 10 μM (which value would be normalized to 100). Alternatively, the reactivity of a compound to be tested can be compared directly to a negative control containing no compound.

The control compound 59-0328, which is simvastatin, gives a good response. The known proteasome inhibitors MG-132 and MG-115 also show high activity; MG-132 is effective at lower concentrations. Positive responses are also obtained using lactacystin. However, gliotoxin, olomoucine, roscovitine, SN50, PDTC, and capsaicin do not give promising responses.

EXAMPLE 2

In vitro Bone Formation

Selected compounds and appropriate controls were assayed in vitro (ex vivo) for bone formation activity (described above in "Techniques for Neonatal Mouse Calvaria Assay (in vitro)"). Histomorphometrical assessments of ex vivo calvaria were carried out using an OsteoMetrics bone morphometry measurement program, according to the manufacturer's instructions. Measurements were determined using either a 10- or 20-fold objective with a standard point counting eyepiece graticule.

New bone formation was determined (using a 10× objective) by measuring the new bone area formed in one field in 3 representative sections of each bone (4 bones per group). Each measurement was carried out ½ field distance from the end of the suture. Both total bone and old bone area were measured. Data were expressed as new bone area in $\mu m^2$.

The results in Example 1 were somewhat imperfectly correlated with the results in this assay. The control compound, simvastatin showed new bone formation in this assay as did MG-132 and lactacystin. MG-115 also showed positive results although less dramatic than those of simvastatin. However, gliotoxin, which appeared negative in the ABA assay of Example 1 did demonstrate the ability to stimulate bone growth. The remaining compounds, olomoucine, roscovitine, SN50, PDTC and capsaicin appeared negative in this assay.

Osteoblast numbers are determined by point counting. The number of osteoblast cells lining the bone surface on both sides of the bone are counted in one field using a 20× objective. Data are expressed as osteoblast numbers/mm of bone surface.

Alkaline phosphatase activity is measured in the conditioned media of the murine organ cultures, using the method described by Majeska, R. J., et al., *Exp Cell Res* (1978) 111:465–465. Conditioned media are incubated at 37° C. for 20 minutes with phosphatase substrate 104 (Sigma) and the reaction stopped with 2 ml of 0.1 M NaOH. Alkaline phosphatase activity is calculated by measuring cleaved substrate at an optical density of 410 nm in a Beckman dual beam spectrophotometer from the OD410 and corrected for protein concentration.

PSI and MG-132 and control compounds/factors bFGF and BMP-2, and a vehicle control were tested in this assay and the calvaria were analyzed histomorphometrically, as described above. Increase in bone area as a function of concentration; the increase in osteoblasts and the enhancement of alkaline phosphatase activity for PSI were measured.

The data show that PSI is as good as, or better than, BMP-2 and bFGF (two "gold standard" agents for bone growth; see Wozney, J., *Molec Reprod Dev* (1992) 32:160–67; WO95/24211) for inducing bone formation.

An additional experiment, pentoxyfilline (PTX) was tested in the foregoing assay. It exhibited the ability to enhance new bone formation in concentrations as low as 0.1 μm. At a concentration of 10 μm, PTX appeared to enhance the new bone are over control by over 100%; at 100 μm, the increase was approximately three (3) times that of control.

EXAMPLE 3

In vivo Calvarial Bone Growth Data

PSI and MG-132 were assayed in vivo according to the procedure described previously (see "In vivo Assay of Effects of Compounds on Murine Calvarial Bone Growth", supra). As a control, simvastatin provided a 1.5 fold increase in the number of osteoblasts.

In one experiment, vehicle control, bFGF and varying doses of PSI were tested in the in vivo calvarial bone growth assay. The results are reported as a measurement of total bone area, % increase in area over vehicle control, and % increase in new bone width as shown below.

| Compound | Total Bone Area ($\mu m^2$) | % Increase* in Bone Area Compared with Control | % Increase[+] in New Bone Width |
|---|---|---|---|
| Control | 0.64 ± 0.03 | | |
| 0.1 mg/kg/day | 0.74 ± 0.02 | 21.7 ± 3.5 | |
| 1 mg/kg/day | 0.83 ± 0.02 | 35.4 ± 3.4 | 19.9 ± 2.0 |
| 5 mg/kg/day | 0.79 ± 0.03 | 32.1 ± 5.6 | 19.9 ± 4.4 |

*$p < 0.05$
[+]$p < 0.001$

In addition, histological examination showed confirmation of bone growth both when 5 mg/kg/day of PSI was used and 1 mg/kg/day was used.

EXAMPLE 4

Summary of Effects on Bone Formation

The table below summarizes the results obtained for compounds tested in the various assays set forth above. It is seen that compounds that are proteasome inhibitors also enhance bone formation. In the compounds tested in this table, however, compounds which are known to be inhibitors only of NF-κB but which fail to inhibit proteasomal activity, do not enhance luciferase activity (indicative of BMP-2 promoter activity) in the high through-put assay, nor do they enhance bone formation in the calvarial assay in vitro, to as great an extent as do proteasome inhibitors.

Compounds useful in the invention include:

| Compound | Structure | Luciferase Activity (ED$_{50}$-µM) | | Bone Formation (ED$_{50}$-µM) | | Proteasome Activity (ED$_{50}$-µM) | |
|---|---|---|---|---|---|---|---|
| Simvastatin | *(structure shown)* | ⇑ | 0.2 | ⇑ | 0.2 | ⇓ | — |
| Lactacystin | *(structure shown)* | ⇑ | 1 | ⇑ | 1 | ⇓ | 1.5 |
| PS1 | Z-lie-Glu(OtBu)-Ala-Leu-CHO | ⇑ | 0.05 | ⇑ | 0.03 | ⇓ | 0.035 |
| MG-132 | *(structure shown)* Z-Leu-Leu-Leu-CHO | ⇑ | 0.25 | ⇑ | 0.5 | ⇓ | 0.3 |
| MG262 | *(structure shown, ending in S(OH)2)* | ⇑ | 0.1 | ⇑ | 0.1 | ⇓ | 0.07 |
| MG115 | *(structure shown)* Z-Leu-Leu-Nva-CHO | ⇑ | 2 | ⇑ | 1 | ⇓ | 1 |

-continued

| Compound | Structure | Luciferase Activity (ED$_{50}$- μM) | | Bone Formation (ED$_{50}$- μM) | | Proteasome Activity (ED$_{50}$- μM) | |
|---|---|---|---|---|---|---|---|
| ALLN | N-Acetyl-Leu-Leu-Nle-CHO | ⇑ | 10 | — | — | ⇓ | 1.5 |
| Cyclosporin A | 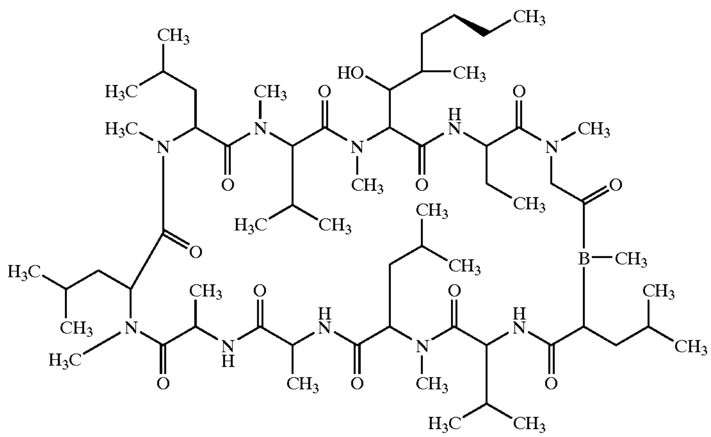 | — | — | ⇑ | 10 | ⇓ | 1.0 |
| Gliotoxin | 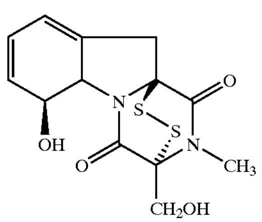 | — | — | ⇑ | 10 | — | — |
| SN50 | NLS of NF-KB MW 2781 N-Acetyl-Leu-Leu-Meth-CHO | — | — | — | — | ⇓ | 4 |
| PPM-18 | 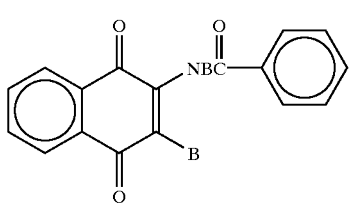 | — | — | — | — | — | — |
| Bay 11-7082 | 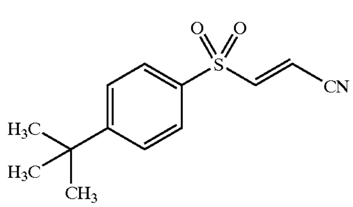 | — | — | — | — | — | — |

-continued

| Compound | Structure | Luciferase Activity (ED$_{50}$- $\mu$M) | | Bone Formation (ED$_{50}$- $\mu$M | Proteasome Activity (ED$_{50}$- $\mu$M) |
|---|---|---|---|---|---|
| Capsaicin | CH$_3$O, HO-phenyl-CH$_2$-NH-C(=O)-(CH$_2$)$_4$-CH=CH-CH(CH$_3$)-CH$_3$ | — | — | — | ⇓ 30 |
| PDTC | pyrrolidine-N-C(=S)-SNH$_4$ | — | — | — | — |

EXAMPLE 5

Confirmation of Proteasomal Inhibition

An assay to test the effect of compounds on the 20S thermophila proteasome activity was employed. Purified 20S thermophila proteasomes and the fluorogenic peptide substrate Suc-Leu-Leu-Val-Tyr-AMC (SEQ ID NO:3) are available from CalBiochem, San Diego, Calif. Briefly, serial dilutions of the inhibitor to be tested were mixed with proteasome solution at a concentration of proteasome of 0.01 mg/ml. After 30 min incubation at 37° C., substrate solution at a final concentration of 25–30 $\mu$g/ml was added and the mixture incubated at 37° C. and then read at 15 min, 30 min, and 60 min in a Fluoroscan instrument. The percentage diminution in fluorescence in the presence as compared to the absence of inhibitor is then calculated.

Epoxomicin, PSI and MG-132 were tested in this assay with the results shown below in Table 1 which sets forth the percent proteasomal activity in the presence of various concentrations of these compounds as compared to untreated control.

TABLE 1

| Dose ($\mu$M) | Epoxomicin % Proteasomal Activity | PSI % Proteasomal Activity | MG-132 % Proteasomal Activity |
|---|---|---|---|
| 2 | — | — | 19 |
| 1 | 5 | 5 | 44 |
| 0.5 | 6 | 6 | 57 |
| .25 | 14 | 11 | 73 |
| 0.125 | 30 | 30 | 87 |
| 0.062 | 51 | 54 | 90 |
| 0.032 | 71 | 76 | 98 |
| 0.016 | 85 | 86 | 100 |
| 0.008 | 95 | 94 | 101 |
| 0.004 | 102 | 95 | 99 |
| 0.002 | 103 | 100 | 101 |

As seen, both epoxomicin and PSI were able to diminish proteasomal activity by approximately 50% at a concentration of about 60 nM. In addition, proteasome inhibitor I (PSI) gave a dose response curve similar to that of epoxomicin.

EXAMPLE 6

Additional High Throughout Assay

The high through-put assay described in Example 1 was performed as an independent experiment to test the activity of epoxomicin, PSI and with simvastatin as a standard positive control. The results of this assay are shown in Table 2.

TABLE 2

| Dose ($\mu$M) | Epoxomicin Luciferase activity/well | PSI Luciferase activity/well | Simvastatin Luciferase activity/well |
|---|---|---|---|
| 10 | — | — | 0.15 |
| 5 | — | — | 0.15 |
| 2.5 | — | — | 0.14 |
| 1.25 | — | — | 0.11 |
| 0.625 | — | — | 0.09 |
| 0.32 | — | — | 0.07 |
| 0.16 | — | — | 0.07 |
| 0.08 | 0.21 | 0.18 | 0.07 |
| 0.04 | 0.20 | 0.12 | 0.07 |
| 0.02 | 0.17 | 0.09 | 0.07 |
| 0.01 | 0.14 | 0.08 | 0.07 |
| 0.005 | 0.10 | 0.08 | 0.07 |
| 0.0025 | 0.08 | 0.07 | 0.065 |
| 0.00125 | 0.07 | 0.08 | 0.07 |
| 0.000625 | 0.07 | 0.07 | 0.07 |

Both epoxomicin and PSI were more active than simvastatin in this assay.

EXAMPLE 7

Activity of Epoxomicin in the Calvarial Assay

The calvarial assay described in Example 3 was performed to test the ability of epoxomicin to stimulate bone growth. The results in terms of new bone area are shown in Table 3. As seen, at a concentrations of 5–10 nM, significantly more bone was formed than in the control.

TABLE 3

| Dose ($\mu$M) | New Bone Area (mm$^2 \times 10^{-3}$) | S. E. M. |
|---|---|---|
| Control | 2.76 | 0.40 |
| 0.01 | 5.74# | 0.27 |
| 0.005 | 6.54# | 0.45 |
| 0.0025 | 4.04 | 0.39 |
| 0.00125 | 2.80 | 0.84 |
| 0.000625 | 2.78 | 0.50 |

EXAMPLE 8

Effect of PSI and Other Proteasome Inhibitors on Hair Follicle Production

The in vivo bone calvarial growth assay of Example 3 was modified to observe the number of hair follicles in treated mice. In initial observations, PSI (5mg/kg/day) was injected three times a day for 5 days over the calvaria of Swiss ICR mice as described above. Sixteen days later the mice were sacrificed. Histology of the calvaria revealed a strikingly large increase in the number of hair follicles in those mice treated with PSI versus control mice. In addition to PSI, MG-132 (10 mg/kg), MG115 (10 mg/kg) and lactacystin administered in the same way also stimulated an increase in the number of hair follicles.

EXAMPLE 9

Stimulation of Hair Growth

Male Swiss ICR mice were first treated to remove hair from the scalp and dorsal regions as follows. Paraffin wax was liquefied by heating to 55° C. and the liquefied wax then applied by brush to the scalp and/or back (under anesthesia). The wax was allowed to solidify and then removed. The day following hair stripping, PSI (1 mg/kg/day) was injected subcutaneously three times a day for five days into the scalp and dorsal region. On day 7 a dermal punch biopsy was taken; histology revealed a large increase in the number of hair follicles in mice administered PSI versus control mice. By day 18, it was observable that the treated mice had a hair growth rate greater than that of the mice in the control group.

The mice were sacrificed on day 21 and histology was performed on the dermis of the scalp and of the dorsal region. In the treated mice, mature hair follicles in numbers much greater than in controls had migrated to the lower region of the dermis. Upon closer examination, it was observed that mice that had received only vehicle had quiescent hair follicles. When treated with PSI such follicles were stimulated to differentiate into mature hair follicles and to migrate to the lower region of the dermis.

EXAMPLE 10

Effects on Subcutaneous Tissue

Effects of PS1 on subcutaneous tissue of the scalp of 6-weeks old ICR mice from longitudinal and transverse sections were determined. PS1 dissolved in 50% propylene glycol, 10% DMSO, and 40% distilled water was injected daily for 5 days (1 mg/kg body weight/day) into the subcutaneous tissue, and the tissue examined histologically 16 days later. The numbers of hair follicles increased and the downward extension of these hair follicles into the dermal tissue (100×) was noted, which are both hallmarks of anagen. There was an obvious increase in size of the follicle diameter and the root sheath diameter (200×).

EXAMPLE 11

Explants

Cultured skin explants from 5 day old mice cultured for 72 hours were treated with proteasome inhibitors, non-proteasomal proteases and non-proteasomal inhibitors of NF-κB and effects on hair follicle diameter and follicle elongation were determined according to the method of Kamiya, T., et al., *J Derm Sci* (1998) 17:54–60. Skin slices from the dorsal skin of 5 day old C3H/HeS1c mice were cultured in 1 ml of αMEM and 0.1% BSA for 72 hours and then assessed for changes in hair follicle diameter and hair elongation under an inverted microscope, using image analysis. The following doses were used—epoxomicin (2.5 nM), PS1-epoxide (12.5 nM), PS1 (12.5 nM), MG-132 (0.5 µM), PDTC (10 µM), and Roscovotine (10 µM). While the NF-κB inhibitor 1-pyrrolidinecarbodithioic acid (PDTC) and the cyclin-dependent kinase inhibitor roscovitine did not significantly affect follicle growth, the proteasome inhibitors lactacystin, PS1, and MG132 effectively stimulated hair follicle differentiation and enhanced hair growth. The epoxyketone-containing natural product epoxomicin, which specifically inhibits the chymotrypsin-like catalytic activity of the proteasome was found to be effective in concentrations as low as 12.5 nM. A hybrid compound that contained the peptide side-chain of PS1 linked to the epoxyketone pharmnacophore of epoxomicin to give it selectivity for the proteasome (PS1-epoxide) selectively inhibits the chymotrypsin-like activity of the proteasome and potently stimulated new hair growth. Thus, the chymotrypsin-like activity of the proteasome is the catalytic component of the proteasome that is responsible for the effects of these compounds on hair follicle differentiation and hair growth. Only proteasome inhibitors had discernable effects on these parameters.

EXAMPLE 12

Anagen Effect

Inhibitors of the proteasomal chymotrypsin-like activity were treated for their capacity to induce transit of hair follicles into anagen in vivo in C57 black mice eight weeks of age. Epoxomicin, PS1 (5 mg/kg/day) or PS1-epoxide (10 mg/kg/day) was injected subcutaneously in the scalp daily for 5 days, and the underlying tissue examined 16 days later. All three compounds increased hair follicle differentiation in vivo. In contrast, NF-κB inhibitors calpain inhibitor-I PDTC and 2-benzoylamino-1,4-naphthoguinone (PPM-18), as well as the statins lovastatin and simvastatin, have no effects on proteasomal activity (Law, R. E, et al., *Mol Cell Biol* (1992) 12:103–111; Guijarro, C., et al., *Nephrol Dial Transplant* (1996) 11:990–996). Lovastatin and simvastatin injected locally into the subcutaneous tissue in sufficient concentrations to cause local periosteal bone formation (Mundy, G., et al., *Science* (1999) 286:1946–1949), had no effect on hair follicles. Calpain inhibitor-I, PDTC and PPM-18 also had no effect on hair follicles.

These data suggest that only those compounds that cause inhibition of proteasome function stimulate induction of anagen in quiescent hair follicles in vivo.

EXAMPLE 13

Topical Administration

PSI was prepared as a topical formulation, where the vehicle was 50% propylene glycol, 30% ethanol, 20% deionized water, at 0.1% concentration of PSI. The solution was applied 3 times a day for 5 days. The mice in a treated group were observed as compared to controls similarly treated with vehicle alone. The results at day 16 showed stimulation of hair growth relative to the controls.

In addition to stimulating hair growth, PSI was able to thicken both the hair and the hair shaft. PSI increases hair count when the follicle area is greater than 0.01 mm². When the protocol above was repeated using a 0.5% solution of PSI in groups containing 5 mice each, the number of hairs per 0.8 mm² was 60 in the treated mice versus about 10 in the control group. The percentage of follicle area in a region of about 0.8 mm was about 30% as an average in the treated group as compared to 15% as an average in the control group.

EXAMPLE 14

Dose Requirements

In order to determine the minimal effective dosage of PSI, when used topically, a dose response curve for PSI was prepared. All experiments were preformed according to current good laboratory practice regulations (21CFR58). The mice were divided into 7 groups, 10 mice each, wherein one group was control treated only with vehicle and groups 1–6 with a series of increasing concentrations of PSI in a vehicle comprising 50% propylene glycol, 30% ethanol, 20% deionized water. The concentrations were 0.006%, 0.012%, 0.025%, 0.05%, 0.11% and 0.5%.

The mice were anesthetized (50 µl Mouse Cocktail containing 3 ml ketamine, 2 ml small animal rompum, 5 ml NaCl), identified by ear punch code, weighed and the hair on the dorsal side removed by waxing as described in Example 6. After waxing, the animals were photographed. On the following day (day 1), 100 µl of PSI at the above concentrations in vehicle was brushed onto the area of removed hair. A similar application of PSI solution was performed daily for an additional 4 days.

On Day 7 mice were anesthetized and a biopsy of the dorsal treatment area taken using a 6 mm dermal punch; the specimens were fixed in 10% buffered formalin and embedded in paraffin wax. Sections were cut using a standard microtome.

Mice were monitored daily for signs of hair growth, and any hair growth was recorded by photography. On day 21 animals were euthanized (75 mg/kg body weight phenobarbital, IP injection), 2 cm hair samples were taken for optical based fiber analysis, and the remaining dorsal treatment area was fixed in 10% buffered formalin for further histological analysis. Analysis included quantification of hair thickness and quantification of mature hair follicles. Results were expressed as the mean=+/−the standard error of the mean. Data were analyzed by repeated measures of analysis of variance followed by the Tukey-Kramer post test P values of <0.05 were considered significant.

The results indicate that the minimal effective dose of PSI is 0.5% applied 1 time a day for 4 days; additional experiments showed that 0.1% of PSI applied topically 3 times a day for 5 days was also effective.

Gross observation of mice receiving an effective dose indicated an enhanced rate of hair growth, a thickening of hair diameter, increase in sheath diameter, and differentiation of quiescent hair follicles into more mature forms.

EXAMPLE 15

Effect Without Depilation

To confirm that the responses described above occurred in the absence of depilation and in other strains of mice, PS1 (0.5%) was applied topically once daily for 5 days to eight week old male C57 BL/6 mice in which the dorsal trunks were shaved but not depilated. For this experiment, the hair of 18 C57 BL/6 mice was carefully clipped the hair from the dorsal trunks. Three groups were tested. One group was treated with PS1 (0.5%) applied topically to the shaved area daily. In the second group, PS1 (1 mg/kg body weight/day) was injected locally into the subcutaneous tissue of the shaved area. These two groups were compared with the third group, which was untreated other than the hair on the dorsal trunk was similarly clipped. Blonde hair dye (extra strength bleach powder and 12% hydrogen peroxide in a 1 to 1 w/v ratio) was applied to the dorsal trunks of all mice on the seventh day in order to make it easier to detect new hair growth represented by appearance in the blonded areas of the natural black hair of the mice associated with induction of melanogenesis. By the sixteenth day, the differences between the treated and the untreated mice were obvious, with black hair appearing on the dorsal trunks of the treated mice receiving either topically applied or injected PS1, indicating the more rapid growth of new hair at the site of drug application in these mice. Transverse sections taken from the dorsal trunks of male C57 BL/6 mice directly from areas of application as well as areas adjacent to and distant from that site showed stimulation of hair sheaths was limited to areas of direct topical application. Transverse sections of skin from the dorsal trunks of these mice showed that PS1 increased both the diameter of the hair and the diameter of the inner and outer root sheath only in the applied areas.

EXAMPLE 16

Effect of Hair Cycle Stage

Skin explants from mice during telogen at 3 weeks of age were cultured for 72 hours, in the presence of proteasome inhibitors, and then the explants were histologically examined. In the untreated control explants, the follicles were few and small. In the explants treated with PSI (50 nM), epoxomicin (25 nM), and the hybrid PS1-epoxide (50 nM), there was an obvious increase in hair follicle diameter, and follicle elongation. Minoxidil also caused these changes, but at concentrations 10,000-fold greater. Since these small follicles resemble the miniaturized follicles seen in male pattern baldness, this suggests these compounds may have the same effects in that situation.

The contents of all documents cited above are expressly incorporated herein to the extent required to understand the invention.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method to enhance bone formation or to treat pathological dental conditions or to treat degenerative joint conditions in a vertebrate animal, which method comprises administering to a vertebrate subject in need of such treatment an effective amount of a compound that inhibits proteasomal activity or that inhibits production of proteasome proteins wherein the compound does not inhibit the isoprenoid pathway.

2. The method of claim 1, wherein the compound inhibits the chymotrypsin-like activity of the proteasome.

3. The method of claim 2, wherein the compound is a peptide having at least 3 amino acids and a C-terminal functional group that reacts with the threonine residue of the chymotrypsin-like catalytic site of the proteasome.

4. The method of claim 3, wherein the c-terminal functional group is selected from the group consisting of an epoxide, a —B(OR)$_2$ group, a —S(OR)$_2$ group and a —SOOR group, wherein R is H, an alkyl ($C_{1-6}$) or an aryl ($C_{1-6}$).

5. The method of claim 4, wherein the functional group is an epoxide that forms a morpholino ring with the threonine residue of the chymotrypsin-like catalytic site of the proteasome.

6. The method of claim 2, wherein the peptide is a peptide α', β'-epoxyketone.

7. The method of claim 6, wherein the peptide α', β'-epoxyketone has at least 4 amino acids.

8. The method of claim 6, wherein the c-terminus amino acid of the peptide α', β'-epoxyketone is a hydrophobic amino acid.

9. The method of claim 8, wherein the hydrophobic amino acid is leucine or phenylalanine.

10. The method of claim 6, wherein the peptide α', β'-epoxyketone has the following formula:

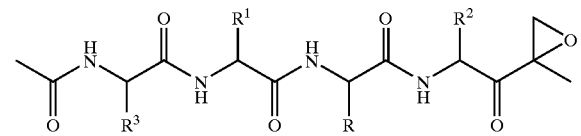

wherein each of R, $R^1$, $R^2$ and $R^3$ is a hydrophobic substituent.

11. The method of claim 10 wherein each of R, $R^1$, $R^2$ and $R^3$ is independently selected from the group consisting of

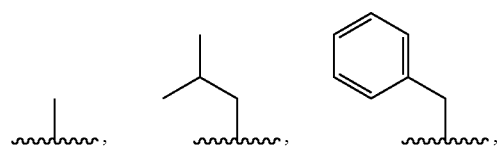

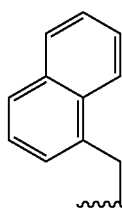, and 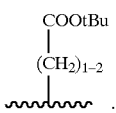.

12. The method of claim 10, wherein $R^2$ and $R^3$ are

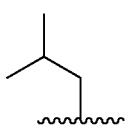

and the compound is selected from the group consisting of compound 1
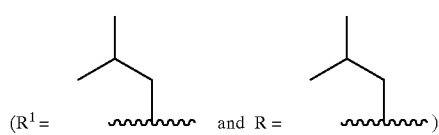
($R^1$ = and R = ), compound 2
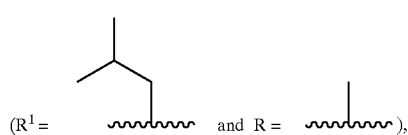
($R^1$ = and R = ), compound 3
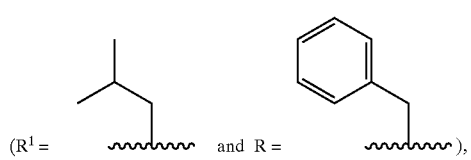
($R^1$ = and R = ), compound 4
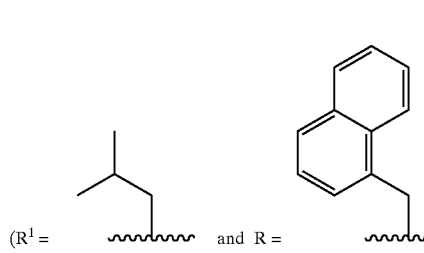
($R^1$ = and R = ), compound 5
($R^1$ = and R = ), compound 6
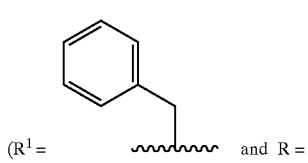
($R^1$ = and R = ) and compound 7
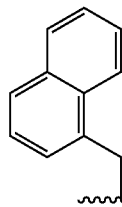
($R^1$ = and R = 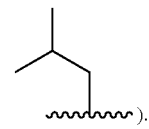).

13. The method of claim 10, wherein the peptide α', β'-epoxyketone has the following stereo-configuration:

$$\text{[structure]}$$

14. The method of claim 6, wherein the peptide α', β'-epoxyketone has the following formula:

$$\text{[structure]}$$

wherein R is selected from the group consisting of

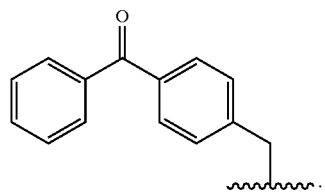

15. The method of claim 14, wherein the peptide α', β'-epoxyketone has the following stereo-configuration:

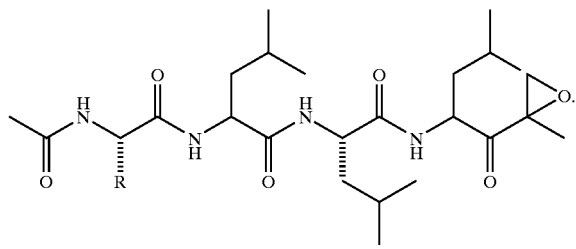

16. The method of claim 15, wherein the peptide α', β'-epoxyketone is

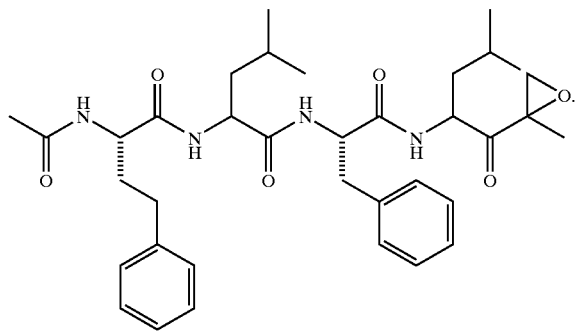

17. The method of claim 2, wherein the compound is selected from the group consisting of

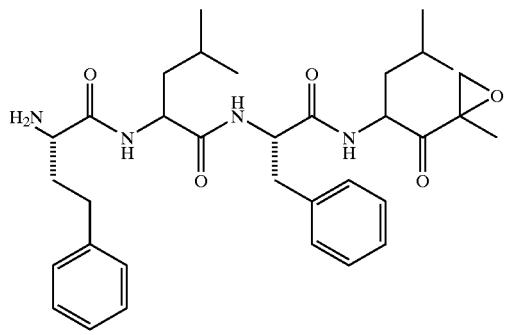

epoxomicin, pyrazylcaarbonyl-Phe-Leu-Boronate (PS-341), tri-leucine vinyl sulfone (NLVS), N-carbobenzoyl-Ile-Glu-(OtBu)-Ala-Leu-CHO (PSI) epoxide, lactacystin, and a peptidyl aldehyde.

18. The method of claim 2, wherein the compound has the following formula:

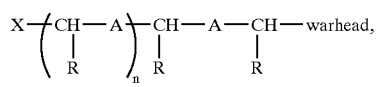

wherein the warhead reacts irreversibly with the catalytic chymotrypsin site of the proteasome;

A is independently CO—NH or isostereomer thereof;

R is independently a hydrocarbyl;

X is a polar group; and n=0–2.

19. The method of claim 18, wherein R contains a substituted group selected from the group consisting of a halo group, —OR, —SR, —NR$_2$, =O, —COR, —OCOR, —NHCOR, —NO$_2$, —CN, and —CF$_3$.

20. The method of claim 18, wherein X is protected.

21. The method of claim 1, wherein the subject is characterized by a condition selected from the group consisting of osteoporosis, bone fracture or deficiency, primary or secondary hyperparathyroidism, periodontal disease or defect, metastatic bone disease, osteolytic bone disease, post-plastic surgery, post-prosthetic joint surgery, and post-dental implantation.

22. The method of claim 1, which further comprises administering to the subject one or more agents that promote bone growth or that inhibit bone resorption.

23. The method of claim 22, wherein the agents are selected from the group consisting of bone morphogenetic factors, anti-resorptive agents, osteogenic factors, cartilage-derived morphogenetic proteins, growth hormones, estrogens, bisphosphonates, statins and differentiating factors.

* * * * *

SEQUENCE LISTING

<160> NUMBER OF SEQ ID NOS: 3

<210> SEQ ID NO 1
<211> LENGTH: 4
<212> TYPE: PRT
<213> ORGANISM: Unknown
<220> FEATURE:
<223> OTHER INFORMATION: a.a. portion of ALLM compound as proteasome
      inhibitor

<400> SEQUENCE: 1

Gly Pro Phe Leu
1

<210> SEQ ID NO 2
<211> LENGTH: 4
<212> TYPE: PRT
<213> ORGANISM: Unknown
<220> FEATURE:
<223> OTHER INFORMATION: a.a. portion of ALLM compound as proteasome
      inhibitor

<400> SEQUENCE: 2

Gly Pro Ala Phe
1

<210> SEQ ID NO 3
<211> LENGTH: 4
<212> TYPE: PRT
<213> ORGANISM: Unknown
<220> FEATURE:
<223> OTHER INFORMATION: fluorogenic peptide substrate

<400> SEQUENCE: 3

Leu Leu Val Tyr
1